(12) United States Patent
Adachi et al.

(10) Patent No.: US 10,294,193 B2
(45) Date of Patent: May 21, 2019

(54) COMPOUND, AND FLAVOR COMPOSITION AND/OR FRAGRANCE COMPOSITION CONTAINING SAME

(71) Applicant: TAKASAGO INTERNATIONAL CORPORATION, Tokyo (JP)

(72) Inventors: Kenichiro Adachi, Kanagawa (JP); Hiroyuki Matsuda, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 15/315,955

(22) PCT Filed: May 28, 2015

(86) PCT No.: PCT/JP2015/065481
§ 371 (c)(1),
(2) Date: Dec. 2, 2016

(87) PCT Pub. No.: WO2015/186614
PCT Pub. Date: Dec. 10, 2015

(65) Prior Publication Data
US 2017/0088503 A1 Mar. 30, 2017

(30) Foreign Application Priority Data
Jun. 4, 2014 (JP) .................... 2014-116076

(51) Int. Cl.
| | |
|---|---|
| *C07C 69/533* | (2006.01) |
| *C07C 209/60* | (2006.01) |
| *C07C 209/88* | (2006.01) |
| *C07C 45/41* | (2006.01) |
| *C07C 47/21* | (2006.01) |
| *C07C 251/40* | (2006.01) |
| *C07C 255/07* | (2006.01) |
| *C07C 43/303* | (2006.01) |
| *C07C 47/02* | (2006.01) |
| *C07C 57/03* | (2006.01) |
| *C07C 33/025* | (2006.01) |
| *C07C 69/145* | (2006.01) |
| *C07C 211/21* | (2006.01) |
| *A61Q 5/02* | (2006.01) |
| *A61Q 19/10* | (2006.01) |
| *A61K 8/33* | (2006.01) |
| *A61K 8/40* | (2006.01) |
| *C11D 3/50* | (2006.01) |
| *C11B 9/00* | (2006.01) |
| *A23L 27/20* | (2016.01) |
| *A23L 2/56* | (2006.01) |
| *A23L 33/10* | (2016.01) |
| *C07B 53/00* | (2006.01) |
| *A61K 8/36* | (2006.01) |
| *A61K 8/37* | (2006.01) |
| *A61Q 13/00* | (2006.01) |

(52) U.S. Cl.
CPC .............. *C07C 69/533* (2013.01); *A23L 2/56* (2013.01); *A23L 27/2024* (2016.08); *A23L 33/10* (2016.08); *A61K 8/33* (2013.01); *A61K 8/36* (2013.01); *A61K 8/37* (2013.01); *A61K 8/40* (2013.01); *A61Q 5/02* (2013.01); *A61Q 13/00* (2013.01); *A61Q 19/10* (2013.01); *C07B 53/00* (2013.01); *C07C 33/025* (2013.01); *C07C 43/303* (2013.01); *C07C 45/41* (2013.01); *C07C 47/02* (2013.01); *C07C 47/21* (2013.01); *C07C 57/03* (2013.01); *C07C 69/145* (2013.01); *C07C 209/60* (2013.01); *C07C 209/88* (2013.01); *C07C 211/21* (2013.01); *C07C 251/40* (2013.01); *C07C 255/07* (2013.01); *C11B 9/0007* (2013.01); *C11B 9/0015* (2013.01); *C11B 9/0019* (2013.01); *C11B 9/0023* (2013.01); *C11D 3/50* (2013.01); *A23V 2002/00* (2013.01); *C07B 2200/07* (2013.01)

(58) Field of Classification Search
None
See application file for complete search history.

(56) References Cited

U.S. PATENT DOCUMENTS

| | | | | |
|---|---|---|---|---|
| 5,800,897 | A * | 9/1998 | Sharma | .................. A61L 9/042 239/53 |
| 6,277,427 | B1 * | 8/2001 | Husz | .................. A23L 2/38 426/590 |
| 6,844,302 | B1 * | 1/2005 | Boden | .................. A23L 27/72 510/101 |
| 2008/0032913 | A1 | 2/2008 | Finke et al. | |
| 2011/0130470 | A1 | 6/2011 | Kraft | |

(Continued)

FOREIGN PATENT DOCUMENTS

| | | |
|---|---|---|
| EP | 1259115 | 11/2002 |
| EP | 2 894 143 A1 | 7/2015 |

(Continued)

OTHER PUBLICATIONS

C.G. Cardenas, H.M. Hoffmann and B.J. Kane. "Isomerization of Dihydromyrcene Oxide", Perfumer and Flavorist, vol. 18, Jan./Feb. 1993, pp. 11-14. (Year: 1993).*

(Continued)

*Primary Examiner* — Michael P Cohen
(74) *Attorney, Agent, or Firm* — Sughrue Mion, PLLC

(57) ABSTRACT

The present invention addresses the problem of providing a novel compound capable of imparting a highly appealing floral and verdant scent, and a flavor composition and/or fragrance composition containing the same. This compound is a racemic or optically active compound represented by general formula (1).

[Chem. 1]

(1)

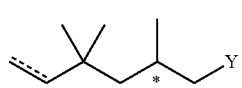

In formula (1), the solid and dotted double line indicates a double bond or a single bond, the definition of Y is the same as described in the specification, and * represents an asymmetric carbon atom.

1 Claim, No Drawings

(56) References Cited

U.S. PATENT DOCUMENTS

2015/0218072 A1 8/2015 Ujihara et al.
2016/0152550 A1 6/2016 Ujihara et al.

FOREIGN PATENT DOCUMENTS

| JP | 2003523370 A | 8/2003 |
| JP | 2011504469 A | 2/2011 |
| JP | 201451461 A | 3/2014 |
| WO | 01/62091 A1 | 8/2001 |
| WO | 2009/065244 A1 | 5/2009 |
| WO | 2014/038665 A1 | 3/2014 |

OTHER PUBLICATIONS

Monograph "Dihydromyrcenol" from the Good Scents Company (downloaded Apr. 23, 2018 from: http://www.thegoodscentscompany.com/data/rw1006052.html). (Year: 2018).*

International Search Report dated Jul. 28, 2015, by the International Searching Authority in counterpart International Application No. PCT/JP2015/065481 (PCT/ISA/210).

Written Opinion dated Jul. 28, 2015, by the International Search Authority in counterpart International Application No. PCT/JP2015/065481 (PCT/ISA/237).

NDSL Canada Gazette, Part I, Jan. 31, 1998. Retrieved from CHEMLIST, No. 53929, CAS Registry No. 72333-11-0, vol. 132, No. 5, 194 pgs. total.

Communication dated Nov. 20, 2017, issued by the European Patent Office in EP application No. 15803317.5.

Feshchenko, et al., "Reaction of Phosphorous Acid with Iodine and Alcohols" Jan. 1966, Journal of General Chemistry of the USSR, vol. 36, No. 1, pp. 162-164, XP9501398.

Communication dated Jan. 10, 2019, issued by the Indian Intellectual Property Office in corresponding Application No. 201647040843.

* cited by examiner

COMPOUND, AND FLAVOR COMPOSITION AND/OR FRAGRANCE COMPOSITION CONTAINING SAME

TECHNICAL FIELD

The present invention relates to a novel compound having a 3,5,5-trimethylheptane structure, a flavor composition and/or fragrance composition containing the compound, a fragrance or cosmetic, toiletry product, bathing agent, beverage, food, quasi drug, or drug containing the flavor composition and/or fragrance composition, and a method for strengthening a scent of a flavor and/or fragrance.

BACKGROUND ART

In recent years, with the diversification of various food ingredients, food additives, beverages, foods (including favorite foods), fragrances or cosmetics, sanitation materials, sundries, drugs, and the like, formerly unknown new demands have been increasing for a flavor and/or fragrance used therein, and development of flavor substance and/or fragrance substance having a highly preferred unique aroma has been requested. In particular, recently, due to the rise in the nature-oriented style of people, with respect to highly preferred floral-like fragrance or green-like fragrance by which the natural environment can be characteristically imaged, development of new fragrance material derived from a natural compound or identical or similar to the natural compound has been strongly desired also from the standpoint of safety.

As a fragrance ingredient having a floral note, homoallylic alcohols (see, for example, Patent Document 1) which are useful as a fragrance can be exemplified.

PRIOR ART DOCUMENT

Patent Document

Patent Document 1: JP-T-2011-504469

SUMMARY OF THE INVENTION

Problems that the Invention is to Solve

However, floral- and green-based flavors and/or fragrances conventionally used are insufficient for expressing scent responding to diversified customer needs, and development of flavor material and/or fragrance material having higher preference has been strongly desired.

Therefore, an object of the present invention is to provide a novel compound capable of imparting floral-like and green-like scents which can satisfy the requirement described above and a flavor composition and/or fragrance composition containing the compound.

Also, another object of the present invention is to provide a product, for example, a fragrance or cosmetic, toiletry product, bathing agent, beverage, food, quasi drug, or drug, which has been imparted with floral-like and green-like scents.

Further, a still another object of the present invention is to provide a method for strengthening floral-like and green-like scents of a flavor and/or fragrance.

Means for Solving the Problems

As a result of the intensive investigations in such circumstances described above, the inventors of the present invention have found that a novel compound having a 3,5,5-trimethylheptane structure has strong floral-like and green-like scents and is able to be a useful scent-imparting agent to complete the present invention.

Specifically, the present invention is achieved by [1] to [7] described below. [1] A racemic or optically active compound represented by the general formula (1) shown below:

[Chem. 1]

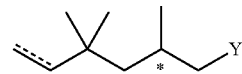

(1)

(in the formula (1), a double line composed of a solid line and a dotted line represents a double bond or a single bond; Y is CHO, $CH(OR^1)(OR^2)$, $CH_2OH$, $CH_2OR^3$, $COOR^4$, $CH=NR^5$, CN, or $CH_2SR^6$; both $R^1$ and $R^2$ are alkyl groups having a carbon number of from 1 to 4 or $R^1$ and $R^2$ may be combined with each other to form a ring; $R^3$ is a hydrogen atom or an acyl group having a carbon number of from 1 to 8; $R^4$ is a hydrogen atom or an alkyl group having a carbon number of from 1 to 4; $R^5$ is a hydroxyl group or a phenyl group which may have a substituent; $R^6$ is a hydrogen atom, an alkyl group having a carbon number of from 1 to 4 or an acyl group having a carbon number of from 1 to 8; and * represents an asymmetric carbon atom).

[2] A flavor composition and/or fragrance composition containing the racemic or optically active compound represented by the general formula (1) as described in [1] above.

[3] A product imparted with a scent, in which the flavor composition and/or fragrance composition as described in [2] above is combined with at least one product selected from the group consisting of beverages, foods, flagrances or cosmetics, toiletry products, air care products, daily necessities and household goods, compositions for oral use, hair care products, skin care products, body care products, detergents for clothing, soft finishing agents for clothing, quasi drugs, and drugs.

[4] A method for improving a scent of a flavor and/or fragrance, including adding the racemic or optically active compound represented by the general formula (1) as described in [1] above.

[5] A method of producing a racemic or optically active aldehyde represented by the formula (1a) shown below:

[Chem. 2]

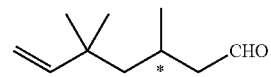

(1a)

(in the formula (1a), * represents an asymmetric carbon atom);

the method including subjecting a triene represented by the formula (2) shown below to an amination in the presence of an alkali metal salt of an amine to obtain an allylamine represented by the general formula (3) shown below:

[Chem. 3]

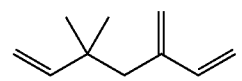

(2)

-continued

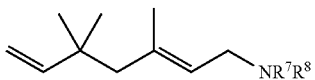
(3)

(in the formula (3), $R^7$ and $R^8$ each independently is a hydrogen atom, an alkyl group having a carbon number of from 1 to 20 which may have a substituent, a cycloalkyl group having a carbon number of from 3 to 8 which may have a substituent, an aryl group which may have a substituent, a heterocyclic group which may have a substituent, or an aralkyl group which may have a substituent, provided that the case where both $R^7$ and $R^8$ are hydrogen atoms is excluded, and $R^7$ and $R^8$ may be connected to each other to form a ring);

subsequently performing an isomerization to obtain a racemic or optically active enamine represented by the general formula (4) shown below:

[Chem. 4]

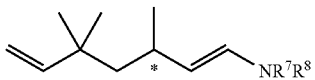
(4)

(in the formula (4), $R^7$ and $R^8$ have the same meanings as defined above; and * represents an asymmetric carbon atom);

and further performing a solvolysis.

[6] An allylamine represented by the general formula (3) shown below:

[Chem. 5]

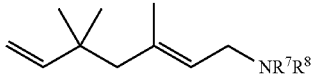
(3)

(in the formula (3), $R^7$ and $R^8$ each independently is a hydrogen atom, an alkyl group having a carbon number of from 1 to 20 which may have a substituent, a cycloalkyl group having a carbon number of from 3 to 8 which may have a substituent, an aryl group which may have a substituent, a heterocyclic group which may have a substituent, or an aralkyl group which may have a substituent, provided that the case where both $R^7$ and $R^8$ are hydrogen atoms is excluded, and $R^7$ and $R^8$ may be connected to each other to form a ring).

[7] A racemic or optically active enamine represented by the general formula (4) shown below:

[Chem. 6]

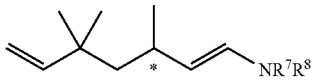
(4)

(in the formula (4), $R^7$ and $R^8$ each independently is a hydrogen atom, an alkyl group having a carbon number of from 1 to 20 which may have a substituent, a cycloalkyl group having a carbon number of from 3 to 8 which may have a substituent, an aryl group which may have a substituent, a heterocyclic group which may have a substituent, or an aralkyl group which may have a substituent, provided that the case where both $R^7$ and $R^8$ are hydrogen atoms is excluded, and $R^7$ and $R^8$ may be connected to each other to form a ring; and * represents an asymmetric carbon atom).

Advantage of the Invention

The racemic or optically active compound represented by general formula (1) according to the present invention is an extremely useful flavor material and/or fragrance material which is highly preferred, excellent in a scent imparting property and excellent in diffusibility and a flavor and/or fragrance remaining property. By blending the compound, a preferred scent imparting agent can be provided.

MODE FOR CARRYING OUT THE INVENTION

The compound according to the present invention is a racemic or optically active compound represented by general formula (1) shown below (hereinafter, also referred to as a "compound having a 3,5,5-trimethylheptane structure of the present invention").

[Chem. 7]

(1)

(In the formula (1), a double line composed of a solid line and a dotted line represents a double bond or a single bond, Y is CHO, $CH(OR^1)(OR^2)$, $CH_2OH$, $CH_2OR^3$, $COOR^4$, $CH=NR^5$, CN, or $CH_2SR^6$, both $R^1$ and $R^2$ are alkyl groups having a carbon number of from 1 to 4 or $R^1$ and $R^2$ may be combined with each other to form a ring, $R^3$ is a hydrogen atom or an acyl group having a carbon number of from 1 to 8, $R^4$ is a hydrogen atom or an alkyl group having a carbon number of from 1 to 4, $R^5$ is a hydroxyl group or a phenyl group which may have a substituent, $R^6$ is a hydrogen atom, an alkyl group having a carbon number of from 1 to 4 or an acyl group having a carbon number of from 1 to 8, and * represents an asymmetric carbon atom.)

The compound represented by general formula (1) is preferably that having a (5S) configuration or a (5R) configuration.

The compound having a 3,5,5-trimethylheptane structure of the present invention can be synthesized, for example, according to the methods illustrated in Scheme 1 and Scheme 2 shown below. However, the synthesis method thereof should not be construed as being limited to the methods of Scheme 1 and Scheme 2 below.

(Scheme 1)

[Chem. 8]

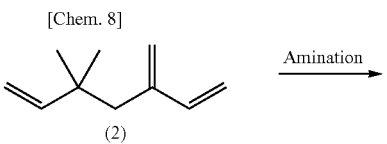 

-continued

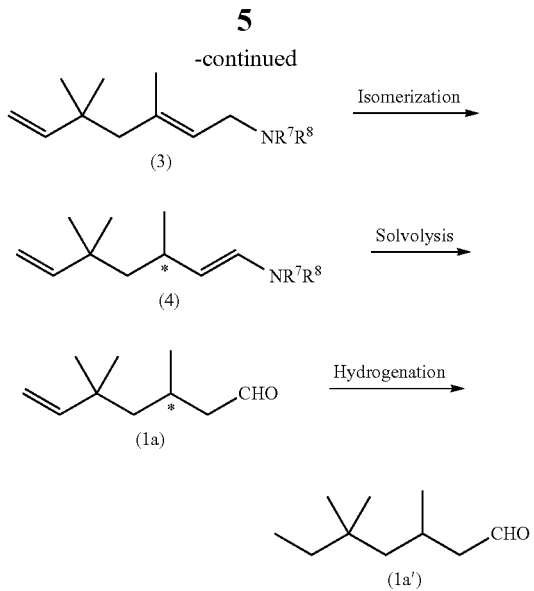

(In formula (3) and formula (4), R[7] and R[8] each independently is a hydrogen atom, an alkyl group having a carbon number of from 1 to 20 which may have a substituent, a cycloalkyl group having a carbon number of from 3 to 8 which may have a substituent, an aryl group which may have a substituent, a heterocyclic group which may have a substituent or an aralkyl group which may have a substituent, provided that the case where both R[7] and R[8] are hydrogen atoms is excluded, and R[7] and R[8] may be connected to each other to form a ring. In formula (4) and formula (1a), * represents an asymmetric carbon atom.)

In Scheme 1, an amination of triene, for example, one represented by formula (2) is performed in the presence of an alkali metal salt of an amine to obtain an allylamine represented by general formula (3) (hereinafter, also referred to as an "allylamine (3)"), an isomerization is then performed to obtain a racemic or optically active enamine represented by general formula (4) (hereinafter, also referred to as an "enamine (4)"), then a solvolysis is performed to obtain a racemic or optically active terminal unsaturated aldehyde represented by formula (1a) (hereinafter, also referred to as a "terminal unsaturated aldehyde (1a)"), and a hydrogenation is performed to obtain a saturated aldehyde represented by formula (1a') (hereinafter, also referred to as a "saturated aldehyde (1a')").

(Scheme 2)

[Chem. 9]

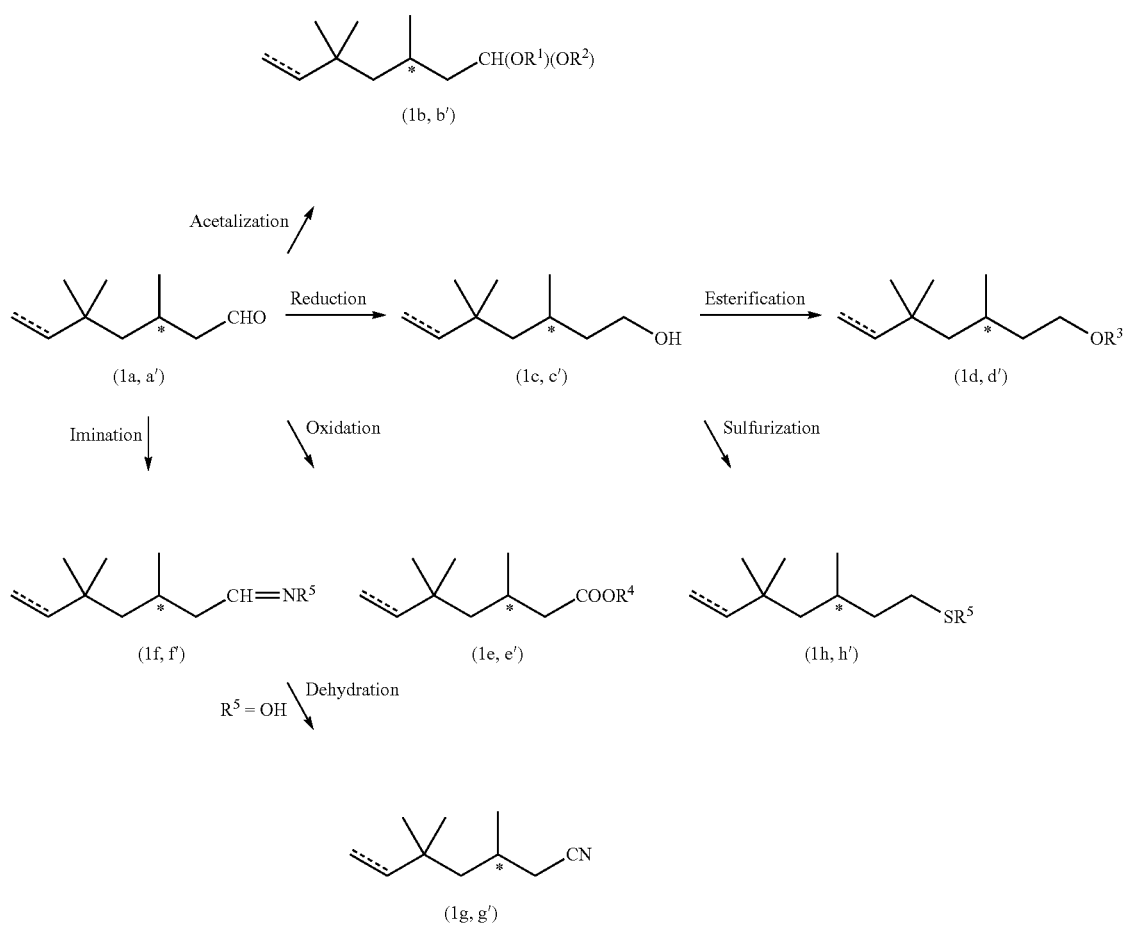

(In the formulae, a double line composed of a solid line and a dotted line represents a double bond or a single bond, and * represents an asymmetric carbon atom. In formula (1b, b'), both $R^1$ and $R^2$ are alkyl groups having a carbon number of from 1 to 4 or $R^1$ and $R^2$ may be combined with each other to form a ring. In formula (1d, d'), $R^3$ is a hydrogen atom or an acyl group having a carbon number of from 1 to 8. In formula (1e, e'), $R^4$ is a hydrogen atom or an alkyl group having a carbon number of from 1 to 4. In formula (1f, f'), $R^5$ is a hydroxyl group or a phenyl group which may have a substituent. In formula (1h, h'), $R^6$ is a hydrogen atom, an alkyl group having a carbon number of from 1 to 4 or an acyl group having a carbon number of from 1 to 8.)

In Scheme 2, by an acetalization of the aldehyde of formula (1a) or (1a') obtained by the method described in Scheme 1, a corresponding acetal of formula (1b) or (1b') can be obtained. Also, by a reduction of an aldehyde portion of the aldehyde of formula (1a) or (1a'), a corresponding alcohol of formula (1c) or (1c') can be obtained. By an esterification of the alcohol thus-obtained, a corresponding ester of formula (1d) or (1d') can be obtained. Moreover, by a conversion of an alcohol portion of the alcohol of formula (1c) or (1c') to mercaptan, a corresponding sulfur-containing compound of formula (1h) or (1h') can be obtained.

On the other hand, by an oxidation of the aldehyde of formula (1a) or (1a'), a corresponding carboxylic acid or a carboxylic acid ester of formula (1e) or (1e') can be obtained. Furthermore, by a condensation of the aldehyde of formula (1a) or (1a') with an amine compound, a corresponding imine of formula (1f) or (1f') can be obtained. Also, by a dehydration treatment of an oxime in which $R^5$ in formula (1f) or (1f') represents a hydroxyl group, a corresponding nitrile of formula (1g) or (1g') can be obtained.

Hereinafter, Scheme 1 and Scheme 2 are specifically described.

The triene represented by formula (2) which is a raw material for producing the compound having a 3,5,5-trimethylheptane structure of the present invention is a known compound and can be produced by a known method, for example, a method described in Yasushi KAJIHARA and other three persons, "Monoterpenoid Synthesis by Transition Metal Catalyzed Coupling of Enediylmagnesium with $C_5$-Organic Halides", The Chemical Society of Japan, 53, 3035-3036 (1980).

An amine which is used for production of the compound having a 3,5,5-trimethylheptane structure of the present invention is described below.

The amine for use in the present invention is represented by general formula (5) shown below.

$$HNR^7R^8 \qquad (5)$$

(In formula (5), $R^7$ and $R^8$ each independently is a hydrogen atom, an alkyl group having a carbon number of from 1 to 20 which may have a substituent, a cycloalkyl group having a carbon number of from 3 to 8 which may have a substituent, an aryl group which may have a substituent, a heterocyclic group which may have a substituent, or an aralkyl group which may have a substituent, provided that the case where both $R^7$ and $R^8$ are hydrogen atoms is excluded, and $R^7$ and $R^8$ may be connected to each other to form a ring.)

The alkyl group having a carbon number of from 1 to 20 represented by $R^7$ or $R^8$ in general formula (5) includes, for example, a methyl group, an ethyl group, a n-propyl group, an isopropyl group, a n-butyl group, an isobutyl group, a sec-butyl group, a tert-butyl group, a n-pentyl group, an iso-pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

The cycloalkyl group having a carbon number of from 3 to 8 represented by $R^7$ or $R^8$ in general formula (5) includes, for example, a cyclopropyl group, a cyclobutyl group, a cyclopentyl group, a cyclohexyl group, a cycloheptyl group, and a cyclooctyl group.

The aryl group represented by $R^7$ or $R^8$ in general formula (5) includes, for example, an aromatic monocyclic or polycyclic group, such as a phenyl group, a naphthyl group, an anthryl group, a phenanthryl group, or an indenyl group. Other examples include a metallocenyl group such as a ferrocenyl group.

The heterocyclic group represented by $R^7$ or $R^8$ in general formula (5) includes, for example, an oxiranyl group, an aziridinyl group, a 2-oxopyrrolidyl group, a piperidyl group, a piperazinyl group, a morpholino group, a tetrahydrofuryl group, a tetrahydropyranyl group, and a tetrahydrothienyl group.

The aralkyl group represented by $R^7$ or $R^8$ in general formula (5) includes, for example, a benzyl group, a 1-phenylethyl group and a 2-phenylethyl group.

In the case where $R^7$ and $R^8$ in general formula (5) are connected to each other to form a ring, it includes, for example, a cyclic amine such as piperidine, pyrrolidine, morpholine, indoline, or isoindoline.

The alkyl group having a carbon number of from 1 to 20, cycloalkyl group having a carbon number of from 3 to 8, aryl group, heterocyclic group, and aralkyl group described above may have a substituent, and the substituent includes, for example, an alkyl group, an aryl group, an aralkyl group, a cycloalkyl group, a halogen atom, a hydroxyl group, an alkoxy group, a tri-substituted organosilyl group, a carboxyl group, an acyl group, an acyloxy group, a substituted amino group, a heterocyclic group, and a nitro group.

The alkyl group as the substituent includes, for example, an alkyl group having a carbon number of from 1 to 6 such as a methyl group, an ethyl group, a n-propyl group, an isopropyl group, a sec-butyl group, a tert-butyl group, a pentyl group, or a hexyl group.

The aryl group as the substituent includes, for example, an aryl group having a carbon number of from 6 to 14 such as a phenyl group, an α-naphthyl group, a β-naphthyl group, an anthryl group, a phenanthryl group, or a biphenyl group.

The aralkyl group as the substituent includes an aralkyl group having a carbon number of from 7 to 12 such as a benzyl group, a 1-phenylethyl group, a 2-phenylethyl group, an α-naphthylmethyl group, or a β-naphthylmethyl group.

The cycloalkyl group as the substituent includes an alicyclic group having a carbon number of from 5 to 8 such as a cyclopentyl group, a cyclohexyl group, a methylcyclohexyl group, a cycloheptyl group, or a cyclooctyl group.

The halogen atom as the substituent includes a fluorine atom, a chlorine atom, a bromine atom, and an iodine atom.

The alkoxy group as the substituent includes an alkoxy group having a carbon number of from 1 to 4 such as a methoxy group, an ethoxy group, a n-propoxy group, an isopropoxy group, a n-butoxy group, an isobutoxy group, a sec-butoxy group, or a tert-butoxy group.

The tri-substituted organosilyl group as the substituent includes a tri(C1 to C6 alkyl)silyl group such as a trimethylsilyl group, a triethylsilyl group, a triisopropylsilyl group, a dimethylisopropylsilyl group, a diethylisopropylsilyl group, a dimethyl(2,3-dimethyl-2-butyl)silyl group, a tert-butyldimethylsilyl group, or a dimethylhexylsilyl group.

The carboxyl group as the substituent includes an alkoxycarbonyl group having a carbon number of from 2 to 6 such as a methoxycarbonyl group or an ethoxycarbonyl group and an arylcarboxyl group having a carbon number of from 6 to 11 such as a phenoxycarbonyl group.

The acyl group as the substituent includes an acyl group having a carbon number of from 1 to 8 such as a formyl group, an acetyl group, a propionyl group, a n-butyroyl group, an isobutyroyl group, or a benzoyl group.

The acyloxy group as the substituent includes an acyloxy group having a carbon number of from 1 to 8 such as a formyloxy group, an acyloxy group, a propionyloxy group, a n-butyroyloxy group, an isobutyroyloxy group, or a benzoyloxy group.

The substituted amino group as the substituent includes a dialkylamino group having alkyl groups each having a carbon number of from 1 to 12 as substituents, such as a dimethylamino group, a diethylamino group, a diisopropylamino group, a piperidyl group, or a piperidyl group.

The heterocyclic group as the substituent includes an aliphatic heterocyclic group and an aromatic heterocyclic group. The aliphatic heterocyclic group includes a 5- to 8-membered, preferably 5- or 6-membered, monocyclic, polycyclic or condensed-cyclic aliphatic heterocyclic group having a carbon number of from 2 to 14 and including, as a heteroatom, at least one, preferably from 1 to 3 heteroatoms, for example, a nitrogen atom, an oxygen atom or a sulfur atom. Specific examples of the aliphatic heterocyclic group include a 2-oxopyrrolidyl group, a piperidyl group, a piperazinyl group, a morpholino group, a tetrahydrofuryl group, a tetrahydropyranyl group and a tetrahydrothienyl group. On the other hand, the aromatic heterocyclic group includes a 5- to 8-membered, preferably 5- or 6-membered, monocyclic, polycyclic or condensed-cyclic aromatic heterocyclic (heteroaryl) group having a carbon number of from 2 to 15 and including, as a heteroatom, at least one, preferably from 1 to 3 heteroatoms such as a nitrogen atom, an oxygen atom or a sulfur atom. Specific examples of the aromatic heterocyclic group include a furyl group, a thienyl group, a pyridyl group, a pyridinyl group, a pyrazinyl group, a pyradazinyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzimidazolyl group, a benzoxazolyl group, and a benzothiazolyl group.

Specific examples of the amine for use in the present invention include dimethylamine, diethylamine, di-n-propylamine, diisopropylamine, cyclohexylamine, piperidine, pyrrolidine, and morpholine.

The used amount of the triene represented by formula (2) relative to the amine is from 1 to 100 times by mole, preferably from 1 to 10 times by mole, of the triene represented by formula (2), relative to the amine.

The alkali metal salt of an amine which can be used in the present invention can be obtained by allowing the amine described above to react with an alkali metal catalyst. As the alkali metal catalyst, an organic lithium compound, lithium metal, an organic sodium compound, sodium metal, an organic potassium compound, or potassium metal can be used, and an organic lithium compound or lithium metal can be preferably used.

The alkali metal salt of an amine which can be used in the present invention can be prepared by using any method. Examples thereof include a method in which one selected from an organic lithium compound, an organic sodium compound and an organic potassium compound is allowed to react with an amine, and a method in which one selected from lithium metal, sodium metal and potassium metal is allowed to react with an amine in the presence of a hydrogen acceptor olefin such as isoprene or styrene.

The organic lithium compound includes, for example, methyllithium, n-butyllithium, sec-butyllithium, t-butyllithium, and phenyllithium. The organic sodium compound includes, for example, methylsodium, n-butylsodium, sec-butylsodium, t-butylsodium, and phenylsodium. The organic potassium compound includes, for example, methylpotassium, n-butylpotassium, sec-butylpotassium, t-butylpotassium, and phenylpotassium.

The amount of the alkali metal catalyst used in the amination is from 0.001 to 1 time by mole, preferably from 0.05 to 0.5 times by mole, relative to the amine used in the reaction.

The amination reaction is performed in an inert atmosphere with or without using a solvent. In the case of using a solvent, a solvent capable of dissolving the alkali metal catalyst is used. The solvent which can be used includes, for example, a hydrocarbon solvent such as benzene or toluene, and an ether solvent such as tetrahydrofuran.

As to the reaction temperature, it cannot be said definitely depending on the raw material and reagent used, and is ordinarily from 0 to 150° C. and preferably from 50 to 100° C.

As to the reaction time, it cannot be said definitely, and is ordinarily from several minutes to 24 hours and preferably from 1 to 10 hours.

After the completion of the reaction, to the reaction mixture obtained by performing the amination of the triene represented by formula (2) in the presence of the alkali metal salt of an amine under the reaction conditions described above is added water, ethanol, carbon dioxide, or the like to deactivate the alkali metal catalyst as the catalyst, and then the oil layer is subjected to a purification treatment, for example, by distillation or column chromatography, thereby obtaining the allylamine represented by general formula (3).

The allylamine is a compound having isomers of (E)-from and (Z)-form.

In the allylamine obtained by the synthesis method of the present invention described above, the (2E)-allylamine (3) which is the (E)-form has an extremely high chemical purity as the (E)-from/(Z)-from ratio of 95/5 to 100/0. Thus, it may be used for the isomerization in the subsequent step without being subjected to fine distillation.

The racemic enamine represented by general formula (4) can be obtained by performing the isomerization of the allylamine (3) obtained by the amination reaction described above.

As a method for isomerization of the allylamine (3), a method for isomerization using a transition metal phosphine complex as a catalyst can be adopted.

As the transition metal phosphine complex which can be used in the present invention, a complex containing a transition metal complex and a phosphine ligand is preferably used.

The phosphine ligand which can be used in the transition metal phosphine complex for isomerization of the allylamine (3) of the present invention includes, for example, a monodentate phosphine ligand, a bidentate phosphine ligand and a polydentate phosphine ligand.

The monodentate phosphine ligand includes a monodentate phosphine ligand represented by general formula (6) shown below.

[Chem. 10]

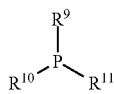
(6)

(In formula (6), $R^9$ to $R^{11}$ each independently represents an alkyl group having a carbon number of from 1 to 10, a cycloalkyl group having a carbon number of from 3 to 8 which may have a substituent or an aromatic group which may have a substituent, or any two of $R^9$, $R^{10}$ and $R^{11}$ may be connected to each other together with the phosphorus atom bound thereto to form a ring.)

In the general formula (6), $R^9$ to $R^{11}$ each independently represents an alkyl group having a carbon number of from 1 to 10, a cycloalkyl group having a carbon number of from 3 to 8 which may have a substituent or an aromatic group which may have a substituent, or any two of $R^9$, $R^{10}$ and $R^{11}$ may be connected to each other together with the phosphorus atom bound thereto to form a ring.

The alkyl group having a carbon number of from 1 to 10 represented by any of $R^9$ to $R^{11}$ in general formula (6) includes, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a hexyl group, a heptyl group, an octyl group, a nonyl group, and a decyl group.

In the cycloalkyl group having a carbon number of from 3 to 8 which may have a substituent, represented by any of $R^9$ to $R^{11}$ in general formula (6), the cycloalkyl group includes, for example, a cyclopropyl group, a cyclobutyl group, a cyclopentyl group, a cyclohexyl group, a cycloheptyl group, and a cyclooctyl group.

In the aromatic group which may have a substituent, represented by any of $R^9$ to $R^{11}$ in general formula (6), the aromatic group includes a hydrocarbon aromatic group such as a phenyl group, a naphthyl group, an anthryl group, a phenanthryl group, or an indenyl group; a heteroaromatic group such as a pyrrolyl group, a pyridyl group, a pyrazyl group, a quinolyl group, an isoquinolyl group, or an imidazolyl group; and a metallocenyl group such as a ferrocenyl group.

Specific examples of the substituent include an alkyl group having a carbon number of from 1 to 12 such as a methyl group, an ethyl group, a n-propyl group, an isopropyl group, a n-butyl group, an isobutyl group, a sec-butyl group, a tert-butyl group, a n-pentyl group, an isopentyl group, a neopentyl group, a hexyl group, a heptyl group, an octyl group, a nonyl group, a decyl group, an undecyl group, or a dodecyl group; a lower alkoxy group having a carbon number of from 1 to 4 such as a methoxy group, an ethoxy group, a n-propoxy group, an isopropoxy group, a n-butoxy group, an isobutoxy group, a sec-butoxy group, or a tert-butoxy group; an aryl group such as a phenyl group, an α-naphthyl group, a β-naphthyl group, or a phenanthryl group; an aralkyl group having a carbon number of from 7 to 13 such as a benzyl group, an α-phenylethyl group, a β-phenylethyl group, an α-phenylpropyl group, a 3-phenylpropyl group, a γ-phenylpropyl group, or a naphthylmethyl group; a tri-substituted organosilyl group including, a tri(C1 to C6 alkyl)silyl group such as a trimethylsilyl group, a triethylsilyl group, a triisopropylsilyl group, a dimethylisopropylsilyl group, a diethylisopropylsilyl group, a dimethyl (2,3-dimethyl-2-butyl)silyl group, a tert-butyldimethylsilyl group, or a dimethylhexylsilyl group, a di(C1 to C6 alkyl) (C6 to C18 aryl)silyl group such as a dimethylcumylsilyl group, a di(C6 to C18 aryl) (C1 to C6 alkyl)silyl group such as a tert-butyldiphenylsilyl group or a diphenylmethylsilyl group, a tri(C6 to C18 aryl)silyl group such as a triphenylsilyl group, and a tri(C7 to 19 aralkyl)silyl group such as a tribenzylsilyl group or a tri-p-xylylsilyl group; a halogen atom such as a fluorine atom, a chlorine atom, a bromine atom, or an iodine atom; and a nitro group.

In the case where any two of $R^9$, $R^{10}$ and $R^{11}$ are connected to each other together with the phosphorus atom bound thereto to form a ring, the ring in which $R^9$ and $R^{10}$, $R^{10}$ and $R^{11}$, or $R^{11}$ and $R^9$ are connected together with the phosphorus atom bound thereto includes rings of a 4-membered ring, a 5-membered ring and a 6-membered ring. Specific rings include a phosphetane ring, a phospholane ring, a phosphorinane ring, a 2,4-dimethylphosphetane ring, a 2,4-diethylphosphetane ring, a 2,5-dimethylphospholane ring, a 2,5-diethylphospholane ring, a 2,6-dimethylphosphane ring, and a 2,6-diethylphosphorinane ring.

Specific examples of the monodentate phosphine ligand represented by the general formula (6) include trimethylphosphine, triethylphosphine, tributylphosphine, triphenylphosphine, tritolylphosphine, tri(3,5-xylyl)phosphine, methyldiphenylphosphine, dimethylphenylphosphine, and phenylphosphorane.

The bidentate phosphine ligand includes a bidentate phosphine ligand represented by general formula (7) shown below.

[Chem. 11]

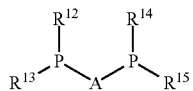
(7)

(In formula (7), $R^{12}$ to $R^{15}$ each independently represents an alkyl group having a carbon number of from 1 to 10, a cycloalkyl group having a carbon number of from 3 to 8 which may have a substituent or an aromatic group which may have a substituent, or $R^{12}$ and $R^{13}$ or $R^{14}$ and $R^{15}$ may be connected to each other together with the phosphorus atom bound thereto to form a ring, and A represents an alkylene chain which may have a substituent, a cycloalkanediyl group which may have a substituent, an alaryldiyl group which may have a substituent, or an aryldiyl group which may have a substituent.)

In the general formula (7), $R^{12}$ to $R^{15}$ each independently represents an alkyl group having a carbon number of from 1 to 10, a cycloalkyl group having a carbon number of from 3 to 8 which may have a substituent or an aromatic group which may have a substituent, or $R^{12}$ and $R^{13}$ or $R^{14}$ and $R^{15}$ may be connected to each other together with the phosphorus atom bound thereto to form a ring, and A represents an alkylene chain which may have a substituent, a cycloalkanediyl group which may have a substituent, an alaryldiyl group which may have a substituent, or an aryldiyl group which may have a substituent.

The alkyl group having a carbon number of from 1 to 10 represented by any of $R^{12}$ to $R^{15}$ in general formula (7) includes the same as that exemplified in general formula (6).

In the cycloalkyl group having a carbon number of from 3 to 8 which may have a substituent, represented by any of $R^{12}$ to $R^{15}$ in general formula (7), the cycloalkyl group includes the same as that exemplified in general formula (6).

In the aromatic group which may have a substituent, represented by any of $R^{12}$ to $R^{15}$ in general formula (7), the aromatic group includes the same as that exemplified in general formula (6).

Specific examples of the substituent described above in general formula (7) include the same as those exemplified in general formula (6).

In the case where $R^{12}$ and $R^{13}$ or $R^{14}$ and $R^{15}$ is connected to each other together with the phosphorus atom bound thereto to form a ring in general formula (7), the ring formed includes the same as those exemplified in general formula (6).

The alkylene chain represented by A in general formula (7) includes, for example, a methylene group, an ethylene group, a trimethylene group, a tetramethylene group, a pentamethylene group, and a hexamethylene group.

The cycloalkanediyl group represented by A in general formula (7) includes, for example, a cyclobutanediyl group, a cyclopentanediyl group, a cyclohexanediyl group, and a cycloheptanediyl group.

The alaryldiyl group represented by A in general formula (7) includes, for example, a toluene-2,α-diyl group, a 1,2-xylene-α,α'-diyl group and a 1,3-xylene-α,α'-diyl group.

The aryldiyl group represented by A in general formula (7) includes, for example, a benzenediyl group, a naphthalenediyl group, an anthracenediyl group, a phenanthrenediyl group, a biphenyldiyl group, a binaphthyldiyl group, 4,4'-bi(1,3-benzodioxole)diyl group, and a ferrocenediyl group.

Each of the alkylene chain, the cycloalkanediyl group, the alaryldiyl group, and the aryldiyl group represented by A in general formula (7) may have a substituent. Examples of the substituent include an alkyl group, an alkoxy group, an aryl group, and a heterocyclic group.

The alkyl group as the substituent includes a straight-chain or branched alkyl group having, for example, a carbon number of from 1 to 15, preferably a carbon number of from 1 to 10, more preferably a carbon number of from 1 to 6, and specific examples thereof include a methyl group, an ethyl group, a n-propyl group, an isopropyl group, a n-butyl group, a s-butyl group, an isobutyl group, a t-butyl group, a n-pentyl group, a neopentyl group, and a n-hexyl group.

The alkoxy group as the substituent includes a straight-chain or branched alkoxy group having, for example, a carbon number of from 1 to 6, and specific examples thereof include a methoxy group, an ethoxy group, a n-propoxy group, an isopropoxy group, a n-butoxy group, a s-butoxy group, an isobutoxy group, a t-butoxy group, a n-pentyloxy group, a neopentyloxy group, and a n-hexyloxy group.

The aryl group as the substituent includes an aryl group having, for example, a carbon number of from 6 to 14, and specific examples thereof include a phenyl group, a naphthyl group, an anthryl group, a phenanthryl group, and a biphenyl group.

The heterocyclic group as the substituent includes an aliphatic heterocyclic group and an aromatic heterocyclic group. The aliphatic heterocyclic group includes a 5- to 8-membered, preferably 5- or 6-membered, monocyclic, polycyclic or condensed-cyclic aliphatic heterocyclic group having, for example, a carbon number of from 2 to 14 and including, as a heteroatom, at least one, preferably from 1 to 3 heteroatoms, for example, a nitrogen atom, an oxygen atom or a sulfur atom. Specific examples of the aliphatic heterocyclic group include a 2-oxopyrrolidyl group, a piperidino group, a piperazinyl group, a morpholino group, a tetrahydrofuryl group, a tetrahydropyranyl group, and a tetrahydrothienyl group. On the other hand, the aromatic heterocyclic group includes a 5- to 8-membered, preferably 5- or 6-membered, monocyclic, polycyclic or condensed-cyclic aromatic heterocyclic (heteroaryl) group having, for example, a carbon number of from 2 to 15 and including, as a heteroatom, at least one, preferably from 1 to 3 heteroatoms such as a nitrogen atom, an oxygen atom or a sulfur atom. Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazinyl group, a quinazolinyl group, a naphthyridinyl group, a cinnolinyl group, a benzimidazolyl group, a benzoxazolyl group, and a benzothiazolyl group.

Specific examples of the bidentate phosphine ligand represented by general formula (7) include bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(diphenylphosphino)benzene, 1,2-bis(anisylphenylphosphino)ethane, 2,3-bis(diphenylphosphino)butane, 1,2-bis(diphenylphosphino)propane, 2,3-bis(diphenylphosphino)-5-norbornene, 2,3-O-isopropylidene-2,3-dihydroxy-1,4-bis(diphenylphosphino)butane, 1-cyclohexyl-1,2-bis(diphenylphosphino)ethane, 2,4-bis-(diphenylphosphino)pentane, 2,2'-bis(diphenylphosphino)-1,1'-bicyclopentane, 2,2'-bis(diphenylphosphino)-1,1'-binaphthyl, 2,2'-bis(diphenylphosphino)-1,1'-(5,5',6,6',7,7',8,8'-octahydrobinaphthyl), 2,2'-bis(di-p-tolylphosphino)-1,1'-binaphthyl, 2,2'-bis(di(3,5-dimethylphenyl)phosphino)-1,1'-binaphthyl, 2,2'-bis(diphenylphosphino)-6,6'-dimethyl-1,1'-biphenyl, (4,4'-bi-1,3-benzodioxole)-5,5'-diylbis(diphenylphosphine), (4,4'-bi-1,3-benzodioxole)-5,5'-diylbis[bis(3,5-dimethylphenyl)phosphine], [(4S)-[4,4'-bi-1,3-benzodioxole]-5,5'-diyl]bis[bis[3,5-bis(1,1-dimethylethyl)-4-methoxyphenyl]phosphine], 2,2'-bis(diphenylphosphino)benzophenone, and 2,2'-bis(di(3,5-dimethylphenyl)phosphino)benzophenone. The bidentate phosphine ligand may be a racemic form or an optically active form.

In the present invention, the optically active enamine represented by general formula (4) can be obtained by performing the asymmetric isomerization of the (E)-allylamine (3) particularly obtained by the amination reaction described above.

In the present invention, as a method for asymmetric isomerization of the (E)-allylamine (3), a method for asymmetric isomerization using an optically active transition metal phosphine complex as a catalyst can be adopted.

As the optically active transition metal phosphine complex which can be used in the present invention, a complex containing a transition metal complex and an optical phosphine ligand is preferably used.

The phosphine ligand which can be used in the optically active transition metal phosphine complex for asymmetric isomerization of (E)-allylamine (3) of the present invention includes, for example, an optically active monodentate phosphine ligand, an optically active bidentate phosphine ligand and an optically active polydentate phosphine ligand, and the optically active bidentate phosphine ligand is preferred.

The optically active bidentate phosphine ligand includes an optically active bidentate phosphine ligand represented by general formula (8) shown below.

[Chem. 12]

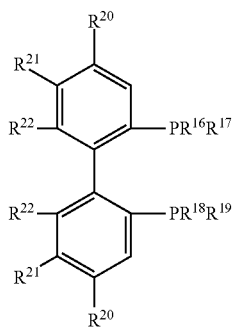

(8)

(In formula (8), $R^{16}$ to $R^{19}$ each independently represents an aromatic group which may have a substituent or a cycloalkyl group having a carbon number of from 3 to 10 which may have a substituent, or each of $R^{16}$ and $R^{17}$ and $R^{18}$ and $R^{19}$ may be connected to each other together with the adjacent phosphorus atom to form a heterocyclic ring; $R^{20}$ and $R^{21}$ each independently represents a hydrogen atom, an alkyl group having a carbon number of from 1 to 5, an alkoxy group having a carbon number of from 1 to 5, a di(C1 to C5 alkyl)amino group, a 5- to 8-membered cyclic amino group, or a halogen atom; and $R^{22}$ represents an alkyl group having a carbon number of from 1 to 5, an alkoxy group having a carbon number of from 1 to 5, a di(C1 to C5 alkyl)amino group, a 5- to 8-membered cyclic amino group, or a halogen atom; plural $R^{20}$s to $R^{22}$s may be the same as or different from each other; or each of $R^{20}$ and $R^{21}$ and $R^{21}$ and $R^{22}$ may be connected to each other to form a condensed benzene ring, a condensed substituted benzene ring, a trimethylene group, a tetramethylene group, a pentamethylene group, a methylenedioxy group, an ethylenedioxy group, or a trimethylenedioxy group.)

In the general formula (8), $R^{16}$ to $R^{19}$ each independently represents an aromatic group which may have a substituent or a cycloalkyl group having a carbon number of from 3 to 10 which may have a substituent, or each of $R^{16}$ and $R^{17}$ and $R^{18}$ and $R^{19}$ may be connected to each other together with the adjacent phosphorus atom to form a heterocyclic ring.

In the aromatic group which may have a substituent, the aromatic group includes, for example, a hydrocarbon aromatic group such as a phenyl group, a naphthyl group, an anthryl group, a phenanthryl group, or an indenyl group; a heteroaromatic group such as a pyrrolyl group, a pyridyl group, a pyrazyl group, a quinolyl group, an isoquinolyl group, or an imidazolyl group; and a metallocenyl group such as a ferrocenyl group.

In the cycloalkyl group having a carbon number of from 3 to 10 which may have a substituent, specific examples of the cycloalkyl group include a cyclopentyl group, a cyclobutyl group, a cyclopentyl group, a cyclohexyl group, a cycloheptyl group, a cyclooctyl group, a cyclononyl group, a cyclodecyl group, and a octahydronaphthyl group.

Specific examples of the substituent, which the aromatic group or the cycloalkyl group having a carbon number of from 3 to 10 may have in formula (8), include an alkyl group having a carbon number of from 1 to 12 such as a methyl group, an ethyl group, a n-propyl group, an isopropyl group, a n-butyl group, an isobutyl group, a sec-butyl group, a tert-butyl group, a n-pentyl group, an isopentyl group, a neopentyl group, a hexyl group, a heptyl group, an octyl group, a nonyl group, a decyl group, an undecyl group, or a dodecyl group; a lower alkoxy group having a carbon number of from 1 to 4 such as a methoxy group, an ethoxy group, a n-propoxy group, an isopropoxy group, a n-butoxy group, an isobutoxy group, a sec-butoxy group, or a tert-butoxy group; an aryl group such as a phenyl group, an α-naphthyl group, a β-naphthyl group, or a phenanthryl group; an aralkyl group having a carbon number of from 7 to 13 such as a benzyl group, an α-phenylethyl group, a β-phenylethyl group, an α-phenylpropyl group, a β-phenylpropyl group, a γ-phenylpropyl group, or a naphthylmethyl group; a tri-substituted organosilyl group including, a tri(C1 to C6 alkyl)silyl group such as a trimethylsilyl group, a triethylsilyl group, a triisopropylsilyl group, a dimethylisopropylsilyl group, a diethylisopropylsilyl group, a dimethyl (2,3-dimethyl-2-butyl)silyl group, a tert-butyldimethylsilyl group, or a dimethylhexylsilyl group, a di(C1 to C6 alkyl) (C6 to C18 aryl)silyl group such as a dimethylcumylsilyl group, a di(C6 to C18 aryl) (C1 to C6 alkyl)silyl group such as a tert-butyldiphenylsilyl group or a diphenylmethylsilyl group, a tri(C6 to C18 aryl)silyl group such as a triphenylsilyl group, and a tri(C7 to 19 aralkyl)silyl group such as a tribenzylsilyl group or a tri-p-xylylsilyl group; a halogen atom such as a fluorine atom, a chlorine atom, a bromine atom, or an iodine atom; and a nitro group.

In the case where each of $R^{16}$ and $R^{17}$ and $R^{18}$ and $R^{19}$ are connected to each other together with the adjacent phosphorus atom to form a heterocyclic ring, specific examples of the heterocyclic group include phosphole, tetrahydrophosphole and phosphorinane. The heterocyclic ring may have one to four functional groups which are inactive in the reaction of the present invention as substituents. Examples of the substituent include an alkyl group having a carbon number of from 1 to 4, an alkoxy group having a carbon number of from 1 to 4 and a halogen atom.

In general formula (8), $R^{20}$ and $R^{21}$ each independently is a hydrogen atom, an alkyl group having a carbon number of from 1 to 5, an alkoxy group having a carbon number of from 1 to 5, a di(C1 to C5 alkyl)amino group, a 5- to 8-membered cyclic amino group, or a halogen atom. Plural $R^{20}$s and $R^{21}$s may be the same as or different from each other, and are preferably the same from the standpoints of economy, superiority in the industry and ease of production.

Specific examples of the alkyl group having a carbon number of from 1 to 5 represented by $R^{20}$ or $R^{21}$ include a methyl group, an ethyl group, a n-propyl group, an isopropyl group, a n-butyl group, an isobutyl group, a sec-butyl group, a tert-butyl group, and a pentyl group.

Specific examples of the alkoxy group having a carbon number of from 1 to 5 represented by $R^{20}$ or $R^{21}$ include a methoxy group, an ethoxy group, a n-propoxy group, an isopropoxy group, a n-butoxy group, an isobutoxy group, a sec-butoxy group, a tert-butoxy group, and a pentoxy group.

Specific examples of the di(C1 to C5 alkyl)amino group represented by $R^{20}$ or $R^{21}$ include a dimethylamino group, a diethylamino group, a di-n-propylamino group, a diisopropylamino group, a di-n-butylamino group, a diisobutylamino group, a di-sec-butylamino group, a di-tert-butylamino group and a dipentylamino group.

Specific examples of the 5- to 8-membered cyclic amino group represented by $R^{20}$ or $R^{21}$ include a pyrrolidino group and a piperidino group.

Specific examples of the halogen atom represented by $R^{20}$ or $R^{21}$ include a fluorine atom, a chlorine atom, a bromine atom and an iodine atom.

Among these, preferred examples of each of $R^{20}$ and $R^{21}$ include a hydrogen atom; an alkyl group having a carbon number of from 1 to 4 such as a methyl group, an ethyl group, a propyl group, an isopropyl group, a n-butyl group, a tert-butyl group, or a trifluoromethyl group; an alkoxy group such as a methoxy group, an ethoxy group, a n-propoxy group, an isopropoxy group, a n-butoxy group, or a tert-butoxy group; a dialkylamino group such as a dimethylamino group or a diethylamino group; and a 5- to 8-membered cyclic amino group such as a pyrrolidino group or a piperidino group.

Each of $R^{20}$ and $R^{21}$ is particularly preferably a hydrogen atom or a methoxy group.

In general formula (8), $R^{22}$s each independently is an alkyl group having a carbon number of from 1 to 5, an alkoxy group having a carbon number of from 1 to 5, a di(C1 to C5 alkyl)amino group, a 5- to 8-membered cyclic amino group, or a halogen atom. $R^{22}$s may be the same as or different from each other, and are preferably the same from the standpoints of economy, superiority in the industry and ease of production.

Specific examples of the alkyl group having a carbon number of from 1 to 5 represented by $R^{22}$ include a methyl group, an ethyl group, a n-propyl group, an isopropyl group, a n-butyl group, an isobutyl group, a sec-butyl group, a tert-butyl group, and a pentyl group.

Specific examples of the alkoxy group having a carbon number of from 1 to 5 represented by $R^{22}$ include a methoxy group, an ethoxy group, a n-propoxy group, an isopropoxy group, a n-butoxy group, an isobutoxy group, a sec-butoxy group, a tert-butoxy group, and a pentoxy group.

Specific examples of the di(C1 to C5 alkyl)amino group represented by $R^{22}$ include a dimethylamino group, a diethylamino group, a di-n-propylamino group, a diisopropylamino group, a di-n-butylamino group, a diisobutylamino group, a di-sec-butylamino group, a di-tert-butylamino group, and a dipentylamino group.

Specific examples of the 5- to 8-membered cyclic amino group represented by $R^{22}$ include a pyrrolidino group and a piperidino group.

Specific examples of the halogen atom represented by $R^{22}$ include a fluorine atom, a chlorine atom, a bromine atom, and an iodine atom.

Among these, preferred examples of $R^{22}$ include an alkyl group having a carbon number of from 1 to 4 such as a methyl group, an ethyl group, a propyl group, an isopropyl group, a n-butyl group, a tert-butyl group, or a trifluoromethyl group; an alkoxy group such as a methoxy group, an ethoxy group, a n-propoxy group, an isopropoxy group, a n-butoxy group, or a tert-butoxy group; a dialkylamino group such as a dimethylamino group or a diethylamino group; and a 5- to 8-membered cyclic amino group such as a pyrrolidino group or a piperidino group.

$R^{22}$ is particularly preferably a methyl group or a methoxy group.

In general formula (8), each of $R^{20}$ and $R^{21}$ and $R^{21}$ and $R^{22}$ may be connected to each other to form a condensed benzene ring, a condensed substituted benzene ring, a trimethylene group, a tetramethylene group, a pentamethylene group, a methylenedioxy group, an ethylenedioxy group, or a trimethylenedioxy group. Among these, it is preferred that $R^{21}$ and $R^{22}$ are connected to each other to form a condensed benzene ring, a condensed substituted benzene ring, a trimethylene group, a tetramethylene group, a pentamethylene group, a methylenedioxy group, an ethylenedioxy group, or a trimethylenedioxy group. It is particularly preferred that $R^{21}$ and $R^{22}$ are connected to each other to form a condensed benzene ring, a condensed substituted benzene ring, a tetramethylene group, a methylenedioxy group, a methylenedioxy group, or an ethylenedioxy group.

In addition, the condensed benzene ring, condensed substituted benzene ring, trimethylene group, tetramethylene group, pentamethylene group, methylenedioxy group, ethylenedioxy group, or trimethylenedioxy group may have, preferably in a number range of from 0 to 4, functional groups which are inactive in the asymmetric synthesis reaction as substituents. Examples of the substituents include an alkyl group having a carbon number of from 1 to 4 such as a methyl group, an ethyl group, a n-propyl group, an isopropyl group, a n-butyl group, an isobutyl group, a sec-butyl group, or a tert-butyl group; a hydroxyl group; an alkoxy group having a carbon number of from 1 to 4 such as a methoxy group, an ethoxy group, a n-propoxy group, an isopropoxy group, n-butoxy group, an isobutoxy group, a sec-butoxy group, or a tert-butoxy group; a halogen atom such as a fluorine atom, a chlorine atom, a bromine atom, or an iodine atom.

Examples of the optically active bidentate phosphine ligand preferably used in the general formula (8) include tertiary phosphines described, for example, in JP-A-58-4749, JP-A-61-63690 and JP-A-62-265293. Specific examples thereof include 2,2'-bis(diphenylphosphino)-1,1'-binaphthyl (BINAP), 2,2'-bis(di(p-tolylphosphino)-1,1'-binaphthyl (Tol-BINAP), 2,2'-bis(di(3,5-xylyl)phosphino)-1,1'-binaphthyl (DM-BINAP), 2,2'-bis(di(3,5-di-tert-butylphenyl)phosphino)-1,1'-binaphthyl (T-Bu-2-BINAP), 2,2'-bis[di(4-methoxy-3,5-dimethylphenyl)phosphino]-1,1'-binaphthyl (DMM-BINAP), 2,2'-bis(dicyclohexylphosphino)-1,1'-binaphthyl (Cy-BINAP), and 2,2'-bis(dicyclopentylphosphino)-1,1'-binaphthyl (Cp-BINAP).

Further, examples of the optically active bidentate phosphine ligand preferably used in the general formula (8) also include tertiary phosphines described, for example, in JP-A-4-139140. Specific examples thereof include 2,2'-bis(diphenylphosphino)-5,5',6,6',7,7',8,8'-octahydrobinaphthyl (H8-BINAP), 2,2'-bis(di-p-tolylphosphino)-5,5',6,6',7,7',8,8'-octahydrobinaphthyl (Tol-H8-BINAP), 2,2'-bis(di-(3,5-xylyl)phosphino)-5,5',6,6',7,7',8,8'-octahydrobinaphthyl (DM-H8-BINAP), and 2,2'-bis(di-(4-methoxy-3,5-dimethylphenyl)phosphino)-5,5',6,6',7,7',8,8'-octahydrobinaphthyl (DMM-H8-BINAP).

Moreover, examples of the optically active bidentate phosphine ligand preferably used in the general formula (8) also include tertiary phosphines described in JP-A-11-269185. Specific examples thereof include ((5,6), (5',6')-bis(methylenedioxy)biphenyl-2,2'-diyl)bis(diphenylphosphine) (SEGPHOS), ((5,6), (5',6')-bis(methylenedioxy)biphenyl-2,2'-diyl)bis(di-p-tolylphosphine) (Tol-SEGPHOS), ((5,6), (5',6')-bis(methylenedioxy)biphenyl-2,2'-diyl)bis(di-3,5-xylylphosphine) (DM-SEGPHOS), ((5,6), (5',6')-bis(methylenedioxy)biphenyl-2,2'-diyl)bis(di-4-methoxy-3,5-dimethylphenylphosphine) (DMM-SEGPHOS), ((5,6), (5',6')-bis(methylenedioxy)biphenyl-2,2'-diyl)bis(di-4-methoxy-3,5-di-tert-butylphenylphosphine) (DTBM-SEGPHOS), and ((5,6), (5',6')-bis(methylenedioxy)biphenyl-2,2'-diyl)bis(dicyclohexylphosphine) (Cy-SEGPHOS).

In addition to the optically active bidentate phosphine ligands described above, the optically active bidentate phosphine ligands which correspond to general formula (8) include 2,2'-dimethyl-6,6'-bis(diphenylphosphino)-1,1'-biphenyl (BIPHEMP), 2,2'-dimethyl-6,6'-bis(di-p-tolylphosphino)-1,1'-biphenyl (Tol-BIPHEMP), 2,2'-dimethyl-6,6'-bis(di-3,5-xylylphosphino)-1,1'-biphenyl (DM-BIPHEMP), 2,2'-dimethyl-6,6'-bis(di-4-methoxy-3,5-dimethylphenylphosphino)-1,1'-biphenyl (DMM-BIPHEMP), 2,2'-dimethyl-6,6'-bis(di-4-t-butoxy-3,5-dimethylphenylphosphino)-

1,1'-biphenyl (DTBM-BIPHEMP), 2,2'-dimethyl-6,6'-bis (dicyclohexylphosphino)-1,1'-biphenyl (Cy-BIPHEMP), 2,2'-dimethoxy-6,6'-bis(diphenylphosphino)-1,1'-biphenyl (MeO-BIPHEP), 2,2'-dimethoxy-6,6'-bis(di-p-tolylphosphino)-1,1'-biphenyl (Tol-MeO-BIPHEP), 2,2'-dimethoxy-6,6'-bis(di-3,5-xylylphosphino)-1,1'-biphenyl (DM-MeO-BIPHEP), 2,2'-dimethoxy-6,6'-bis(di-4-methoxy-3,5-dimethylphenylphosphino)-1,1'-biphenyl (DMM-MeO-BIPHEP), 2,2'-dimethoxy-6,6'-bis(di-4-t-butoxy-3,5-dimethylphenylphosphino)-1,1'-biphenyl (DTBM-MeO-BIPHEP), 2,2'-dimethoxy-6,6'-bis(dicyclohexylphosphino)-1,1'-biphenyl (Cy-MeO-BIPHEP), 2,2'-dimethyl-3,3'-dichloro-4,4'-dimethyl-6,6'-bis(di-p-tolylphosphino)-1,1'-biphenyl (Tol-CM-BIPHEMP), 2,2'-dimethyl-3,3'-dichloro-4,4'-dimethyl-6,6'-bis(di-3,5-xylylphosphino)-1,1'-biphenyl (DM-CM-BIPHEMP), and 2,2'-dimethyl-3,3'-dichloro-4,4'-dimethyl-6,6'-bis(di-4-methoxy-3,5-dimethylphenylphosphino)-1,1'-biphenyl (DMM-CM-BIPHEMP).

In the present invention, an asymmetric hydrogenation reaction is performed by using an optically active transition metal complex composed of the optically active bidentate phosphine ligand described above and a transition metal. The optically active transition metal complex in the asymmetric hydrogenation reaction preferably include, for example, optically active rhodium complexes represented by general formula (9) and general formula (10) shown below.

(In formula (9), olefin is ethylene, 1,3-butadiene, cyclooctadiene, norbornadiene, or cycloocta-1,5-diene, X is $ClO_4$, $BF_4$, $PF_6$, or $PCl_6$, and L is an optically active bidentate phosphine ligand.)

(In formula (10), X and L have the same meanings as defined above, respectively.)

A method for producing the optically active rhodium complex represented by general formula (9) or general formula (10) is not particularly limited, and it can be produced by using, for example, the method shown below or a method based thereon. In the formulae of the transition metal-phosphine complexes shown below, "cod" represents cycloocta-1,5-diene and "nbd" represents norbornadiene.

As to a specific example of production of the optically active rhodium complex, it can be synthesized by allowing chloro(1,5-cyclooctadiene)rhodium (I) dimer ([Rh(cod)Cl]$_2$), silver perchlorate and the optically active bidentate phosphine ligand described above to react according to any of the methods described in JP-A-58-4748, JP-A-59-20294 and JP-A-60-61587.

Specific examples of the rhodium complex are shown below.

The optically active rhodium complex represented by general formula (9) includes [Rh(cod)(L)]OTf, [Rh(cod)(L)]BF$_4$, [Rh(cod)(L)]ClO$_4$, [Rh(cod)(L)]SbF$_6$, [Rh(cod)(L)]PF$_6$, [Rh(cod)(L)]BPh$_4$, [Rh(nbd)(L)]OTf, [Rh(nbd)(L)]BF$_4$, [Rh(nbd)(L)]ClO$_4$, [Rh(nbd)(L)]SbF$_6$, [Rh(nbd)(L)]PF$_6$, and [Rh(nbd)(L)]BPh$_4$.

The optically active rhodium complex represented by general formula (10) includes [Rh(L)$_2$]OTf, [Rh(L)$_2$]BF$_4$, [Rh(L)$_2$]ClO$_4$, [Rh(L)$_2$]SbF$_6$, [Rh(L)$_2$]PF$_6$, and [Rh(L)$_2$]BPh$_4$.

Since each of these optically active bidentate phosphine ligands includes the (−)-form and the (+)-form, it is only necessary to select one of these forms based on the desired absolute configuration of the optically active farnesyl enamine (4). Specifically, in the case of using the (E)-form as the substrate, and, for example, when Tol-BINAP is used as the ligand, in order to obtain the optically active enamine (4) in the (+)-form, the Tol-BINAP in the (−)-form may be used, whereas in order to obtain the optically active farnesyl enamine (4) in the (S)-form, Tol-BINAP in the (+)-form may be used. On the other hand, in the case of using the (Z)-form as the substrate, in order to obtain the optically active farnesyl enamine (4) in the (−)-form, Tol-BINAP in the (+)-form may be used, whereas in order to obtain the optically active farnesyl enamine (4) in the (+)-form, Tol-BINAP in the (−)-form may be used.

The used amount of the transition metal-optically active phosphine complex is preferably approximately from 1/100 to 1/50000 mole relative to the allylamine (3).

As to the reaction solvent, any appropriate one can be used, as long as it is capable of dissolving the raw material and the catalyst system of the asymmetric isomerization. For example, use can be made of an aromatic hydrocarbon solvent such as toluene or xylene; an aliphatic hydrocarbon solvent such as pentane or hexane; a halogen-containing hydrocarbon solvent such as methylene chloride; an ether solvent such as diethyl ether, diisopropyl ether, diethylene glycol dimethyl ether, tetrahydrofuran, or 1,3-dioxolane; an alcohol solvent such as methanol, ethanol, 2-propanol, butanol, or benzyl alcohol; and an organic solvent containing a heteroatom such as acetonitrile, DMF or DMSO. An ether solvent or a mixture solvent with an ether solvent is preferably used.

The used amount of the reaction solvent is determined based on the solubility of the reaction substrate and economy. For example, the reaction can be conducted in a range from a low concentration of 1% or less to an almost non-solvent state depending on the substrate, but the solvent is preferably used in an amount from 0.1 to 5.0 times by volume. As to the reaction temperature, the reaction can be conducted from 0 to 150° C., and more preferably in a range from 70 to 120° C. The reaction time varies depending on the reaction conditions such as the concentration of the reaction substrate, the temperature or the pressure, and the reaction is completed in several minutes to 30 hours. After the completion of the reaction, the desired optically active enamine (4) can be isolated by performing an ordinary after-treatment.

The racemic or optically active enamine represented by formula (4) and obtained by the isomerization described above is an unprecedented novel compound, and is ordinarily in oil from and storable. Therefore, the racemic or optically active enamine (4) obtained by the addition reaction described above may be subjected to a purification treatment, for example, by distillation or a column chromatography treatment and stored or may be stored without performing the purification treatment, and then taken out from a storage container and used at the production in subsequent step.

The terminal unsaturated aldehyde represented by formula (1a) can be obtained by performing the solvolysis of the enamine (4) obtained by the isomerization described above.

As the method for the solvolysis described above, an ordinary known or well-known method for solvolysis of an enamine can be used. The method includes, for example, a method in which the reaction is performed in a solvent by using a catalytic amount or an equivalent mole or more of an inorganic acid or organic acid. The inorganic acid or organic acid used in the solvolysis includes, for example, hydrofluoric acid, hydrochloric acid, hydrobromic acid, sulfuric acid, phosphoric acid, methanesulfonic acid, p-toluenesulfonic acid, acetic acid, chloroacetic acid, trifluoroacetic acid, and an acidic ion-exchange resin. As preferred inorganic acid or organic acid, hydrochloric acid, sulfuric acid, p-toluenesulfonic acid, and the like are preferred because these are inexpensive and versatile, and achieve a high reaction selectivity and a high yield. These inorganic acids and organic acids can be used alone as one kind, or can be used as a mixture of two or more kinds, but a method using one kind is preferred.

The solvent used for the solvolysis may be any one, as long as the solvolysis proceeds with the solvent. Examples thereof include water, an alcohol such as methanol, ethanol or isopropanol, and a mixture solvent thereof. Among them, water, methanol and ethanol are preferred, because these are inexpensive and versatile, and achieve a high reaction selectivity and a high yield.

Moreover, if desired, an auxiliary solvent may be used. As the auxiliary solvent, any one may be used, as long as the solvent does not participate in the reaction. Examples thereof include an organic solvent including an ether solvent such as diethyl ether, diisopropyl ether, tetrahydrofuran, dimethoxyethane, or dioxane, a hydrocarbon solvent such as hexane, heptane or octane, and an aromatic solvent such as benzene, toluene or xylene.

The used amount of the solvent is ordinarily from 0.5 to 100 times in volume, preferably from 1 to 30 times in volume relative to 1 part by mass of the optically active enamine (4) from the standpoints of economy, superiority in the industry and ease of production. The reaction is conducted ordinarily at a temperature approximately from 0 to 250° C., preferably at a temperature approximately from 20 to 100° C., and the reaction is completed by performing it ordinarily for approximately from 10 minutes to 20 hours, preferably for approximately from 30 minutes to 10 hours. The conditions can be modified appropriately depending on the solvent used and the amounts of the catalyst and the like.

After the completion of the reaction, the desired product can be isolated by performing an ordinary after-treatment by employing, if desired, a method such as distillation or column chromatography. Moreover, the reaction in the present invention can be carried out in a batchwise mode or in a continuous mode.

In the case of the optically active enamine (4) in the present reaction, as to the configuration of the asymmetric carbon atom at the 3-position of the optically active enamine (4), the configuration of the optically active enamine (4) is maintained. For example, in the case where the (+)-enamine (4) is used, (−)-terminal unsaturated aldehyde (1a) can be obtained while maintaining the optical purity. Specifically, the configuration of the optically active terminal unsaturated aldehyde (1a) is controlled by the configuration of the optically active ligand used in the asymmetric isomerization reaction.

The racemic or optically active terminal unsaturated aldehyde (1a) obtained by the solvolysis described above is an unprecedented novel compound, and is stable, ordinarily in oil form and storable.

The compounds having a 3,5,5-trimethylheptane structure of the present invention can be synthesized by performing treatments a) to h) shown below using the terminal unsaturated aldehyde (1a) obtained as described above.
a) $H_2$, Pd/C (Hydrogenation)
b) $H^+$, alcohol (Acetalization)
c) $NaBH_4$ (Reduction)
d) Base, acid anhydride or acid halide (Esterification)
e) $H_2O_2$, NaClO (Oxidation), $H^+$, alcohol (Esterification)
f) Halogenation→thiol compound (Sulfurization)
g) Acid catalyst, amine or base, $(NH_3OH)_2SO_4$ (Imination)
h) $Ac_2O$ (Dehydration)

As illustrated in Scheme 1, first, in the terminal unsaturated aldehyde (1a) obtained by the synthesis method described above, the double bond portion is reduced by hydrogenation using Pd/C to obtain the saturated aldehyde (1a').

Next, as illustrated in Scheme 2, the terminal unsaturated aldehyde (1a) or the saturated aldehyde (1a') (hereinafter, collectively referred to as an "aldehyde (1a, a')" in sometimes) is allowed to react with an alcohol under an acidic condition to obtain an acetal (1b, b'). Also, the aldehyde (1a, a') is reduced with sodium borohydride to obtain an alcohol (1c, c'). The alcohol (1c, c') obtained is allowed to react with an acid anhydride or an acid chloride in the presence of a base to obtain an ester (1d, d'). Moreover, the aldehyde (1a, a') is oxidized with hydrogen peroxide or sodium hypochlorite to form a carboxylic acid, followed by a reaction with an alcohol in the presence of an acid catalyst to obtain a carboxylic acid ester (herein, the carboxylic acid and carboxylic acid ester are collectively referred to as (1e, e')).

Furthermore, the aldehyde (1a, a') is treated with an amine in the presence of an acid catalyst to obtain an imine (1f, f). In order to obtain an oxime in which $R^5$ is a hydroxyl group, the aldehyde (1a, a') is allowed to react with hydroxylammonium sulfate in the presence of a base to obtain an oxime (1f, f': R=OH). The oxime (1f, f': R=OH) obtained is treated with acetic anhydride to convert to a nitrile (1g, g').

The compound having a 3,5,5-trimethylheptane structure of the present invention thus-obtained can be subjected to isolation and purification, if desired. A method of the isolation and purification includes, for example, column chromatography or reduced pressure distillation. These are performed individually or in combination thereof.

The compound having a 3,5,5-trimethylheptane structure of the present invention has green-like and floral-like scents.

The compound having a 3,5,5-trimethylheptane structure of the present invention includes R-form and S-form stereoisomers depending on the configuration at the 3-position. Both of the optical isomers have good scents. The R-form and S-form compounds of the present invention can be obtained by using the (−)-from and (+)-form of the optically active ligands, respectively, in the asymmetric isomerization reaction described above.

A flavor composition and/or fragrance composition can be prepared by further adding an ordinarily used flavor component and/or fragrance component to the compound having a 3,5,5-trimethylheptane structure of the present invention. The other flavor components and/or fragrance components to be added and used include various synthetic aromachemicals, natural essential oils, artificial essential oils, citrus oils, animal flavors and/or fragrances. For example, a wide range of flavor components and/or fragrance components as described in the references shown below can be used.

Representative examples of the flavor component and/or fragrance component include α-pinene, limonene, cis-3-hexenol, phenylethyl alcohol, styralyl acetate, eugenol, rose oxide, linalool, benzaldehyde, methyl dihydrojasmonate, and Thesaron (registered trademark, produced by Takasago International Corp.). In addition, the flavor components and/or fragrance components described in Arctander S., "Perfume and Flavor Chemicals", published by the author, Montclair, N.J. (U.S.A.), 1969 can also be exemplified.

When the compound having a 3,5,5-trimethylheptane structure of the present invention is added to natural essential oil such as bergamot oil, galbanum oil, lemon oil, geranium oil, lavender oil, or mandarin oil, a novel fragrance composition for fragrances or cosmetics can be prepared which provides in addition to the aroma and flavor originally possessed by the natural essential oil, mildness, richness, freshness and high preference and has enhanced diffusibility and retention property and good sustainability.

According to the present invention, one kind or two or more kinds of ordinarily used other fragrance fixatives may be blended in the compound having a 3,5,5-trimethylheptane structure or the fragrance composition for fragrances or cosmetics of the present invention, and for example, ethylene glycol, propylene glycol, dipropylene glycol, glycerol, hexyl glycol, benzyl benzoate, triethyl citrate, diethyl phthalate, HERCOLYN (methyl abietate), or a middle-chain fatty acid triglyceride is able to be used in combination.

Products to which the aroma is imparted by fragrancing using the compound having a 3,5,5-trimethylheptane structure or the fragrance composition containing the compound of the present invention are not particularly limited, and include, for example, beverages; foods; toiletry products such as cleaning agents, kitchen detergents or bleaching agents; air care products such as deodorants or air fresheners; compositions for oral use; fragrances or cosmetics such as fragrance products, foundation cosmetics, finish cosmetics, hair cosmetics, suntan cosmetics, or medicated cosmetics; hair care products; skin care products such as soaps; body care products such as body cleaning agents; bath additives; detergents for clothing; soft finishing agents for clothing; aerosols; sundry goods; quasi drugs; and drugs.

Various forms can be exemplified as follows. The beverages described above include, for example, drinks such as fruit juice drinks, fruit wines, milk drinks, carbonated drinks, refreshing drinks, or health drinks; tea drinks or favorite drinks such as green tea, oolong tea, black tea, persimmon leaf tea, chamomile tea, low striped bamboo tea, mulberry tea, dokudami tea, pu-erh tea, mate tea, rooibos tea, gymnema tea, guava tea, coffee, or cocoa; soups such as Japanese style soup, Western style soup or Chinese soup; and various instant drinks. The foods described above include, for example, frozen sweets such as ice creams, sherbets or ice candies; desserts such as jelly or pudding; Western style confections such as cake, cookie, chocolate, or chewing gum; Japanese style confections such as steamed bean-jam bun, sweet beans jelly or sweet rice jelly; jams; candies; breads; flavoring and seasoning; various instant foods; and various snack foods. The compositions for oral use described above include, for example, toothpaste, mouth cleansing agent, mouthwash, troche, and chewing gums. The fragrance products described above includes, for example, perfume, eau de perfume, eau de toilette, and eau de cologne. The foundation cosmetics described above include, for example, facial cleansing cream, banishing cream, cleansing cream, cold cream, massage cream, milky lotion, skin lotion, beauty lotion, pack, and makeup remover. The finishing cosmetics described above include, for example, foundation, face powder, solid face powder, talcum powder, lipstick, lip cream, cheek rouge, eye liner, mascara, eye shadow, eyebrow pencil, eye pack, nail enamel, and enamel remover. The hair cosmetics described above include, for example, pomade, brilliantine, set lotion, hair stick, hair solid, hair oil, hair treatment, hair cream, hair tonic, hair liquid, hair spray, bandoline, revitalizing hair tonic, and hair dye. The suntan cosmetics described above include, for example, suntan products and sunscreen products. The medicated cosmetics described above include, for example, antiperspirant, after shaving lotion or gel, permanent wave agent, medicated soap, medicated shampoo, and medicated skin cosmetics. The hair care products described above include, for example, shampoo, rinse, rinse-in-shampoo, conditioner, treatment, and hair pack. The soaps described above include, for example, toilet soap, bath soap, perfume soap, transparent soap, and synthetic soap. The body cleaning agents described above include, for example, body soap, body shampoo, hand soap, and face cream. The bath additives described above include, for example, bathing agents (for example, bath salt, bath tablet or bath liquid), foam bath (for example, bubble bath), bath oil (for example, bath perfume or bath capsule), milk bath, bath jelly, and bath cube. The detergents described above include, for example, heavy detergent for clothing use, light detergent for clothing use, liquid detergent, laundry soap, compact detergent, and powder soap. The soft finishing agents described above include, for example, softener and furniture care. The cleaning agents described above include, for example, cleanser, house cleaner, toilet cleaner, bath cleaner, glass cleaner, mildew remover, and cleaner for drainpipe use. The kitchen detergents described above include, for example, kitchen soap, kitchen synthetic soap and dishwashing detergent. The bleaching agents described above include, for example, oxidation type bleaching agent (for example, chlorine-based bleaching agent or oxygen-based bleaching agent), reduction type bleaching agent (sulfur-based bleaching agent), and optical bleaching agent. The aerosols described above include, for example, spray type and powder spray. The deodorants or air fresheners described above include, for example, solid type, gel type and liquid type (aqueous or oily). The sundry goods described above include, for example, tissue paper and toilet paper. The quasi drugs described above include, for example, liquid bathing agent, mouthwash and repellent, the repellent includes mist spray type and aqueous liquid type. The drugs described above include, for example, medicated cosmetics and medicated lotion.

As to a dosage form of the compound having a 3,5,5-trimethylheptane structure of the present invention, it can be provided in the form of the mixture itself, and other dosage forms include, for example, a liquid form obtained by dissolving in an alcohol, a polyhydric alcohol such as propylene glycol, glycerol or dipropylene glycol, or an ester such as triethyl citrate, benzyl benzoate or diethyl phthalate; a natural rubber form such as gum arabic or tragacanth gum; an emulsified form obtained by emulsifying with an emulsifier such as glycerol fatty acid ester or sucrose fatty acid ester; a powder form obtained by coating using a carrier such as a natural rubber such as gum arabic, gelatin, or dextrin; a solubilized or dispersed form obtained by solubilizing or dispersing using a surfactant, for example, a nonionic surfactant, an anionic surfactant, a cationic surfactant, or an amphoteric surfactant; or a microcapsule form obtained by treating with an encapsulation agent. Any form can be selected and used, depending on the intended use.

The flavor composition and/or fragrance composition described above may also be used after having been included in an inclusion agent such as cyclodextrin in order to impart stability and sustained release property thereto. It may be appropriately selected and used among ones suitable for the form of the final product, for example, liquid, solid, powder, gel, mist, or aerosol.

EXAMPLES

The present invention will be described specifically with reference to the Examples, but the present invention should not be construed as being limited thereto. Also, various changes or modifications may be added without departing from the scope of the present invention. With respect to the unit of the prescription described below, "%" means "% by mass" and a composition ratio represents a mass ratio, unless otherwise particularly stated.

For the measurement of physical properties in the Examples, apparatuses shown below were used.
NMR: DRX 500 (produced by Bruker Co., Ltd.)
GC/MS: HP5973 (produced by Hewlett Packard Co.)
Column: Capillary column "InertCap 1" (length 30 m×inner diameter 0.25 mm, film thickness 0.25 μm) produced by GL Science Inc.
GC purity: HP6890 (produced by Hewlett Packard Co.)
Column: Capillary column "InertCap 1" (length 30 m×inner diameter 0.25 mm, film thickness 0.25 μm) produced by GL Science Inc.
Injection temperature: 250° C.
Detector temperature: 250° C.
Elevation of temperature at 10° C./min from 100° C. to 200° C.
Polarimeter: P-1020 (produced by JASCO Corp.)

[Synthesis Example 1] Synthesis of N,N-diethyl-3,5,5-trimethylhepta-2,6-diene-1-amine

[Chem. 13]

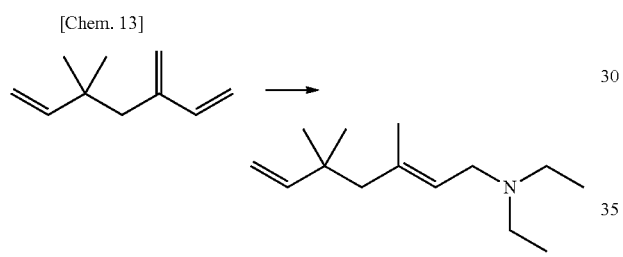

Into a 20-ml flask equipped with a Teflon (registered trademark) made rotor and purged with nitrogen was put 4.29 g (0.0587 mol) of diethylamine, followed by stirring at 5° C. Then, 3.7 ml (1.6 mol/L, 0.0587 mol) of hexane solution of n-butyl lithium was added thereto, followed by stirring at 5° C. for 10 minutes to form a lithium diethylamide solution.

A 30-ml pressure-resistant ampoule was purged with nitrogen, and 2.67 g (0.0196 mol) of 5,5-dimethyl-3-methylene-1,6-heptadiene was added thereto, followed by stirring at 15° C. for 10 minutes. Next, the lithium diethylamine solution described above was added thereto over a period of 5 minutes, followed by heating with stirring at 70° C. for 4 hours.

After the completion of the reaction, 40 ml of toluene was added thereto, followed by washing with 8 ml of water. Subsequently, toluene was first distilled off by Claisen distillation, and the resulting condensate was distilled to purify, thereby obtaining 3.14 g (0.015 mol) of N,N-diethyl-3,5,5-trimethylhepta-2,6-diene-1-amine shown by the formula above in a yield of 77%.

<Physical data of N,N-diethyl-3,5,5-trimethylhepta-2,6-diene-1-amine>
GC/MS m/z (%): 208 (2), 194 (8), 140 (61), 124 (11), 110 (6), 86 (53), 69 (88), 58 (100), 41 (40).
$^1$H NMR (500 MHz, CDCl$_3$) δ: 1.00 (6H, s), 1.03 (6H, t), 1.63-1.64 (3H, m), 2.03 (2H, s), 2.52 (4H, q), 3.06-3.07 (2H, m), 4.88-4.90 (2H, m), 5.20-5.13 (1H, m), 5.82-5.88 (1H, m).

$^{13}$C NMR (125 MHz, CDCl$_3$) δ: 11.8, 19.0, 27.1, 27.1, 30.9, 37.5, 46.7, 46.7, 50.6, 53.1, 109.7, 125.7, 135.4, 149.1.

[Synthesis Example 2] Synthesis of N,N-diethyl-3,5,5-trimethylhepta-1,6-diene-1-amine

[Chem. 14]

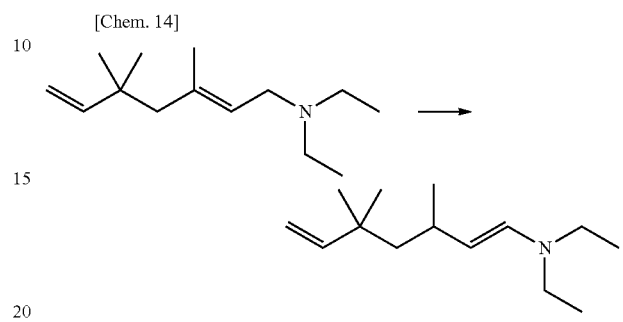

Into a 500-ml pressure resistant reaction vessel equipped with a Teflon (registered trademark) made rotor and purged with nitrogen were charged N,N-diethyl-3,5,5-trimethylhepta-2,6-diene-1-amine (82.0 g) obtained by the method of Synthesis Example 1, tetrahydrofuran (29.6 ml) and a 0.02 mol/L tetrahydrofuran solution of [Rh{(−)-T-binap}$_2$]ClO$_4$ (19.6 ml), followed by heating on an oil bath set at 140° C. and initiating stirring. After heating with stirring for 8 hours, the content was taken out, and solvent recovery was performed under a reduced pressure, thereby obtaining 80.6 g (purity: 73.3%) of crude N,N-diethyl-3,5,5-trimethylhepta-1,6-diene-1-amine shown by the formula above.

Physical data of N,N-diethyl-3,5,5-trimethylhepta-1,6-diene-1-amine

GC/MS m/z (%): 208 (1), 194 (3), 140 (2), 126 (35), 110 (7), 99 (11), 82 (8), 69 (14), 56 (28), 41 (100).
$^1$H NMR (500 MHz, CDCl$_3$) δ: 0.95 (3H, d), 0.99 (3H, s), 1.01 (3H, s), 1.03 (6H, t), 1.30-1.33 (2H, m), 2.11-2.16 (1H, m), 2.91 (4H, q), 4.05-4.09 (1H, m), 4.84-4.88 (2H, m), 5.72-5.75 (1H, m), 5.81-5.86 (1H, m).
$^{13}$C NMR (125 MHz, CDCl$_3$) δ: 12.3, 12.3, 25.4, 27.1, 28.1, 32.3, 37.3, 44.4, 44.4, 51.6, 107.6, 109.3, 135.1, 149.7.

[Synthesis Example 3] Synthesis of (+)-3,5,5-trimethylhept-6-enal

[Chem. 15]

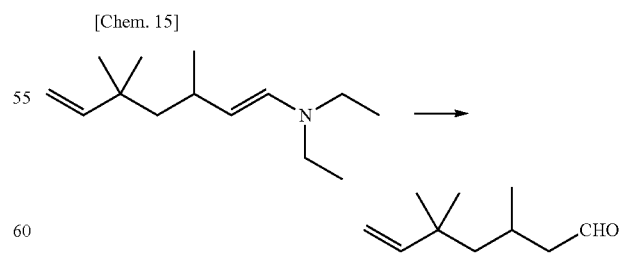

Into a 2,000-ml four-necked flask was charged a 10% aqueous sulfuric acid (921.9 g) under nitrogen stream, followed by initiating stirring and cooling by an ice bath. While maintaining the internal temperature from 18 to 24° C., the crude N,N-diethyl-3,5,5-trimethylhepta-1,6-diene-1- amine (160.7 g) obtained by the method of Synthesis Example 2 was dropwise added thereto, followed by stirring at the internal temperature from 20 to 25° C. for 3 hours. Into the reaction solution was poured n-hexane (328 ml), and after stirring for 5 minutes, the aqueous layer portion was separated. The aqueous layer portion was extracted twice with n-hexane (164 ml), the extract was put together with the first organic layer, washed with a 2% aqueous sulfuric acid (164 g) and further washed twice with water (328 ml). After performing solvent recovery under a reduced pressure, the resulting condensate was distilled to purify (using "HELI PACK No. 2" produced by TO-TOKU Engineering Corp. as a packing, filling height: 12 cm×φ2.5 cm), thereby obtaining 52.4 g (purity: 99.6%) of (+)-3,5,5-trimethylhept-6-enal shown by the formula above.

Physical data of (+)-3,5,5-trimethylhept-6-enal

GC/MS m/z (%): 153 (1), 139 (6), 121 (8), 110 (20), 95 (45), 83 (14), 69 (100), 55 (34), 41 (7).
$^1$H NMR (500 MHz, CDCl$_3$) δ: 0.97 (3H, d), 1.02 (3H, s), 1.02 (3H, s), 1.24-1.37 (2H, m), 2.09-2.11 (1H, m), 2.19-2.24 (1H, m), 2.40-2.44 (1H, m), 4.91-4.95 (2H, m), 5.75-5.81 (1H, m), 9.70 (1H, m).
$^{13}$C NMR (125 MHz, CDCl$_3$) δ: 22.5, 24.9, 27.1, 27.5, 37.1, 49.6, 52.7, 110.6, 148.4, 203.0.
Specific rotation: $[α]_D^{20}$=+6.334 (c=8.1, ethanol)

[Synthesis Example 4] Synthesis of N,N-diethyl-3,5,5-trimethylhepta-1,6-diene-1-amine

[Chem. 16]

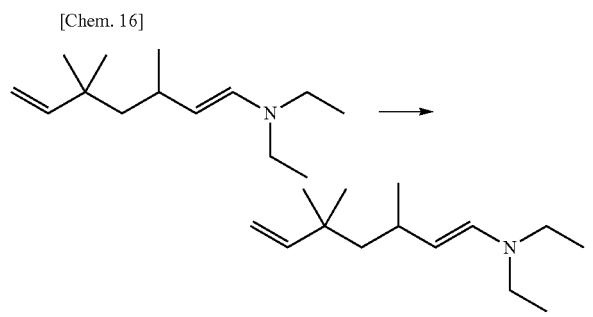

Into a 100-ml pressure resistant reaction vessel equipped with a Teflon (registered trademark) made rotor and purged with nitrogen were charged N,N-diethyl-3,5,5-trimethylhepta-2,6-diene-1-amine (10.0 g) obtained by the method of Synthesis Example 1, tetrahydrofuran (6.2 ml) and a 0.02 mol/L tetrahydrofuran solution of [Rh{(+)-T-binap}$_2$]ClO$_4$ (2.0 ml), followed by heating on an oil bath set at 95° C. and initiating stirring. After heating with stirring for 43 hours, the content was taken out, and solvent recovery was performed under a reduced pressure, thereby obtaining 9.6 g (purity: 29.2%) of crude N,N-diethyl-3,5,5-trimethylhepta-1,6-diene-1-amine shown by the formula above.

Physical data of N,N-diethyl-3,5,5-trimethylhepta-1,6-diene-1-amine

GC/MS m/z (%): 208 (1), 194 (3), 140 (2), 126 (35), 110 (7), 99 (11), 82 (8), 69 (14), 56 (28), 41 (100).
$^1$H NMR (500 MHz, CDCl$_3$) δ: 0.95 (3H, s), 0.99 (3H, s), 1.01 (3H, s), 1.03 (6H, t), 1.30-1.33 (2H, m), 2.11-2.16 (1H, m), 2.91 (4H, q), 4.05-4.09 (1H, m), 4.84-4.88 (2H, m), 5.72-5.75 (1H, m), 5.81-5.86 (1H, m).
$^{13}$C NMR (125 MHz, CDCl$_3$) δ: 12.3, 12.3, 25.4, 27.1, 28.1, 32.3, 37.3, 44.4, 44.4, 51.6, 107.6, 109.3, 135.1, 149.7.

[Synthesis Example 5] Synthesis of (−)-3,5,5-trimethylhept-6-enal

[Chem. 17]

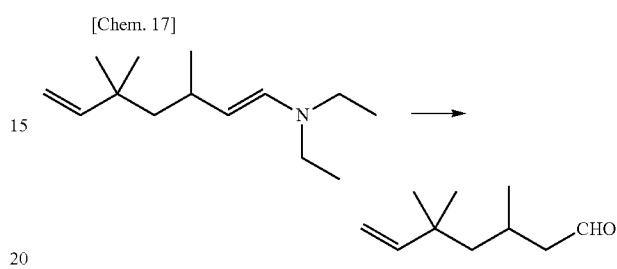

Into a 100-ml four-necked flask were charged a 10% aqueous sulfuric acid (29.0 g) and n-hexane (20 ml) under nitrogen stream, followed by initiating stirring and cooling by an ice bath. While maintaining the internal temperature at 10° C. or less, the crude N,N-diethyl-3,5,5-trimethylhepta-1,6-diene-1-amine (9.6 g) obtained in Synthesis Example 4 was dropwise added thereto, followed by stirring at room temperature for 3 hours. After separating the aqueous layer portion of the reaction solution, the organic layer was washed three times with water (20 ml). After performing solvent recovery under a reduced pressure, the resulting condensate was purified by silica gel column chromatography, thereby obtaining 1.4 g (purity: 96.9%) of (−)-3,5,5-trimethylhept-6-enal shown by the formula above.

Physical data of (−)-3,5,5-trimethylhept-6-enal 153 (1), 139 (6), 121 (8), 110 (20), 95 (45), 83 (14), 69 (100), 55 (34), 41 (7).
$^1$H NMR (500 MHz, CDCl$_3$) δ: 0.97 (3H, d), 1.02 (3H, s), 1.02 (3H, s), 1.24-1.37 (2H, m), 2.09-2.11 (1H, m), 2.19-2.24 (1H, m), 2.40-2.44 (1H, m), 4.91-4.95 (2H, m), 5.75-5.81 (1H, m), 9.70 (1H, m).
$^{13}$C NMR (125 MHz, CDCl$_3$) δ: 22.5, 24.9, 27.1, 27.5, 37.1, 49.6, 52.7, 110.6, 148.4, 203.0.
Specific rotation: $[α]_D^{20}$=−6.232 (c=8.0, ethanol)

[Synthesis Example 6] Synthesis of 3,5,5-trimethylhept-6-enal oxime

[Chem. 18]

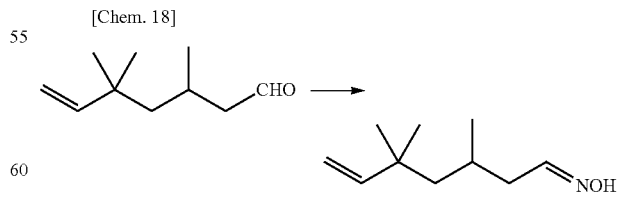

Into a 100-ml three-necked flask were charged the (+)-3,5,5-trimethylhept-6-enal (2.0 g) obtained in Synthesis Example 3, hydroxylammonium sulfate (1.4 g) and water (10 ml) under nitrogen stream, followed by initiating stirring and cooling by an ice bath. To the mixture was dropwise added a 50% aqueous sodium hydroxide (1.3 g), followed by stirring for one hour while cooling with ice. To the reaction solution were added toluene (10 ml) and water (5 ml), followed by stirring for 5 minutes to dissolve the salt formed, and the aqueous layer portion was separated. The organic layer was washed twice with water (10 ml), and then solvent recovery was performed under a reduced pressure, thereby obtaining 1.6 g (purity: 95.6%, equal amount mixture of E form and Z form) of 3,5,5-trimethylhept-6-enal oxime shown by the formula above.

Physical data of 3,5,5-trimethylhept-6-enal oxime

GC/MS m/z (%): 168 (1), 154 (15), 137 (6), 126 (5), 110 (14), 95 (16), 83 (9), 69 (100), 55 (39), 41 (80).
$^1$H NMR (500 MHz, CDCl$_3$) δ: 0.93-0.96 (3H, m), 1.00 (3H, d), 1.01 (3H, s), 1.18-1.26 (1H, m), 1.34-1.39 (1H, m), 1.67-1.78 (1H, m), 1.99-2.05 (0.5H, m), 2.16-2.26 (1H, m), 2.34-2.39 (0.5H, m), 4.89-4.94 (2H, m), 5.75-5.82 (1H, m), 6.72 (0.5H, t), 7.38 (0.5H, t), 8.13 (0.5H, s), 8.52 (0.5H, s).

[Synthesis Example 7] Synthesis of 3,5,5-trimethyhept-6-ene nitrile

[Chem. 19]

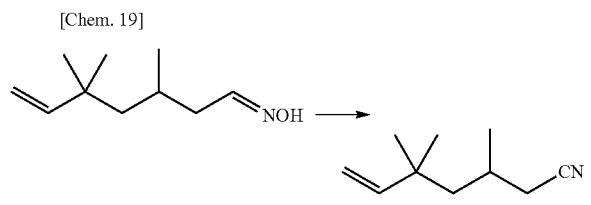

Into a 50-ml two-necked flask was charged acetic anhydride (0.9 g) under nitrogen stream, followed by heating on an oil bath set at 110° C. and initiating stirring. To the mixture was dropwise added 3,5,5-trimethylhept-6-enal oxime (1.5 g) obtained in Synthesis Example 6 suspended in toluene (3 ml), followed by heating with stirring for 30 minutes. Into another 100-ml flask was charged a 5% aqueous sodium carbonate (22 g), and the reaction solution described above was dropwise added thereto while maintaining the internal temperature at 10° C. or less by cooling with an ice bath. After the dropwise addition, n-heptane (15 ml) was added thereto, followed by stirring for 5 minutes, and the aqueous layer portion was separated. The organic layer was washed with water (10 ml), and then solvent recovery was performed under a reduced pressure. The resulting condensate was purified by silica gel column chromatography, thereby obtaining 0.8 g (purity: 98.0%) of 3,5,5-trimethylhept-6-ene nitrile shown by the formula above.

Physical data of 3,5,5-trimethylhept-6-ene nitrile

GC/MS m/z (%): 150 (2), 136 (15), 108 (17), 94 (12), 83 (11), 69 (100), 55 (41), 41 (87).
$^1$H NMR (500 MHz, CDCl$_3$) δ: 1.02 (3H, s), 1.03 (3H, s), 1.08 (3H, d), 1.31-1.35 (1H, m), 1.42-1.46 (1H, m), 1.84-1.93 (1H, m), 2.22-2.34 (2H, m), 4.93-4.97 (2H, m), 5.76-5.82 (1H, m).
$^{13}$C NMR (125 MHz, CDCl$_3$) δ: 22.0, 26.0, 26.6, 27.2, 27.9, 36.9, 48.5, 111.2, 119.0, 147.8.

[Synthesis Example 8] Synthesis of 7,7-diethoxy-3,5,5-trimethylhept-1-ene

[Chem. 20]

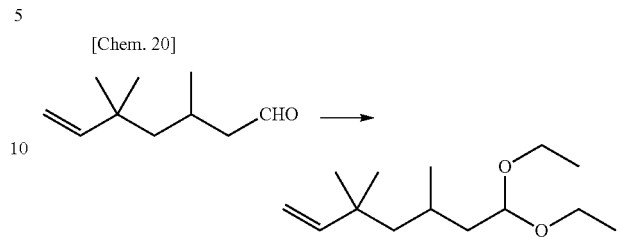

Into a 300-ml four-necked flask were charged, under nitrogen stream, ethanol (30 ml), ethyl acetate (10 ml), para toluenesulfonic acid (0.06 g), and the (+)-3,5,5-trimethylhept-6-enal (2.0 g) obtained in Synthesis Example 3, and a distillation column filled with "HELI PACK No. 2" (trade name, produced by TO-TOKU Engineering Corp., 12 cm×φ2.5 cm) was installed, followed by heating on an oil bath set at 125° C. and initiating stirring. After confirming the initiation of reflux, 20 ml of the azeotropic mixture was distilled off while maintaining the column top temperature at 75° C. or less. The reaction solution was cooled to the internal temperature of 40° C., and an aqueous 5% sodium hydrogen carbonate solution (3 g) was added thereto to neutralize, followed by performing solvent recovery. The condensate was diluted with n-heptane (20 ml), washed with water (10 ml), and then solvent recovery was performed under a reduced pressure. The resulting condensate was purified by silica gel column chromatography, thereby obtaining 1.78 g (purity: 99.4%) of 7,7-diethoxy-3,5,5-trimethylhept-1-ene shown by the formula above.

Physical data of 7,7-diethoxy-3,5,5-trimethylhept-1-ene

GC/MS m/z (%): 227 (1), 199 (2), 183 (2), 167 (4), 137 (66), 121 (11), 103 (100), 95 (75), 75 (99), 69 (81), 47 (98), 41 (94).
$^1$H NMR (500 MHz, CDCl$_3$) δ: 0.92 (3H, d), 1.00 (3H, s), 1.00 (3H, s), 1.15-1.19 (1H, m), 1.18-1.21 (6H, m), 1.32-1.41 (2H, m), 1.58-1.65 (2H, m), 3.43-3.51 (2H, m), 3.57-3.67 (2H, m), 4.53 (1H, m), 4.87-4.92 (2H, m), 5.77-5.83 (1H, m).
$^{13}$C NMR (125 MHz, CDCl$_3$) δ: 15.3, 15.4, 22.6, 25.8, 27.1, 27.6, 37.1, 42.6, 50.3, 60.1, 61.2, 101.6, 109.9, 149.0.

[Synthesis Example 9] Synthesis of 3,5,5-trimethylheptanal

[Chem. 21]

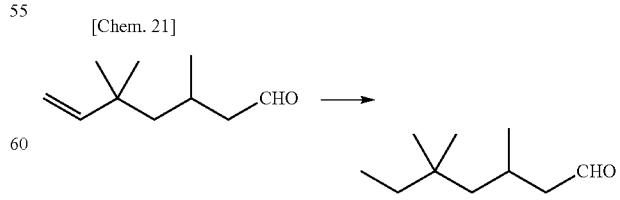

The reaction was performed by using a flow type hydrogenation apparatus "H-CUBE PRO" produced by ThalesNano Inc. and a 5% palladium carbon catalyst cartridge "THS 08112" produced by ThalesNano Inc. Specifically, a 0.2 mol/L n-hexane solution (32 ml) of the (+)-3,5,5-trimethylhept-6-enal obtained in Synthesis Example 3 was prepared, and subjected to raw material feed, that is, supply at a flow rate of 2.0 ml/min under normal temperature and normal pressure, thereby preparing a hydrogenation reaction solution (purity excluding solvent: 89.1%). This was purified by silica gel column chromatography, thereby obtaining 0.12 g (purity: 99.7%) of 3,5,5-trimethylheptanal shown by the formula above.

Physical data of 3,5,5-trimethylheptanal

GC/MS m/z (%): 123 (14), 109 (39), 97 (15), 83 (72), 71 (92), 55 (52), 43 (100).

$^1$H NMR (500 MHz, CDCl$_3$) δ: 0.81 (3H, t), 0.86 (6H, s), 1.01 (3H, d), 1.12-1.18 (2H, m), 1.21-1.29 (2H, m), 2.14-2.18 (1H, m), 2.24-2.29 (1H, m), 2.38-2.42 (1H, m), 9.74 (1H, m).

$^{13}$C NMR (125 MHz, CDCl$_3$) δ: 8.4, 22.9, 24.3, 26.9, 27.0, 33.6, 34.8, 48.4, 53.3, 203.2.

[Synthesis Example 10] Synthesis of 3,5,5-trimethylhept-6-enic acid

[Chem. 22]

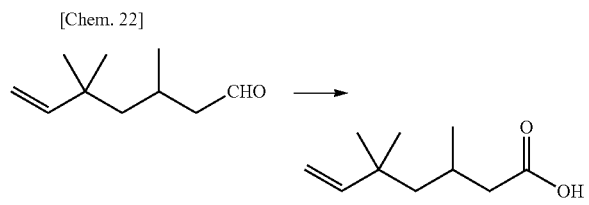

Into a 300-ml four-necked flask were charged the (+)-3,5,5-trimethylhept-6-enal (10.0 g) obtained in Synthesis Example 3, disodium hydrogen phosphate (1.6 g), a 35% hydrogen peroxide solution (6.3 g), water (20.5 g), and acetonitrile (75 ml) under nitrogen stream, followed by initiating stirring and cooling by an ice bath. An aqueous solution containing 79% sodium chlorite (10.4 g) dissolved in water (70 ml) was dropwise added thereto, followed by stirring for 1.5 hours while maintaining the internal temperature at 20° C. or less. To the reaction solution was added little by little sodium sulfite (4.0 g) to deactivate the oxidizing agent, n-heptane (50 ml) and a 10% aqueous hydrochloric acid (45 ml) were added thereto, and after mixing for 5 minutes, the aqueous layer portion was separated. The organic layer was washed with water (20 ml), and then solvent recovery was performed under a reduced pressure, thereby obtaining 8.3 g (purity: 85.7%) of 3,5,5-trimethylhept-6-enic acid shown by the formula above.

Physical data of 3,5,5-trimethylhept-6-enic acid

GC/MS m/z (%): 169 (1), 137 (5), 125 (6), 111 (19), 95 (27), 83 (12), 69 (98), 55 (45), 41 (100).

$^1$H NMR (500 MHz, CDCl$_3$) δ: 0.98 (3H, d), 1.01 (3H, s), 1.02 (3H, s), 1.23-1.27 (1H, m), 1.35-1.39 (1H, m), 1.97-2.04 (1H, m), 2.09-2.14 (1H, m), 2.37-2.42 (1H, m), 4.90-4.95 (2H, m), 5.76-5.82 (1H, m).

$^{13}$C NMR (125 MHz, CDCl$_3$) δ: 22.2, 26.9, 27.3, 37.0, 43.1, 49.4, 110.5, 148.5, 179.2.

[Synthesis Example 11] Synthesis of allyl 3,5,5-trimethylhept-6-enoate

[Chem. 23]

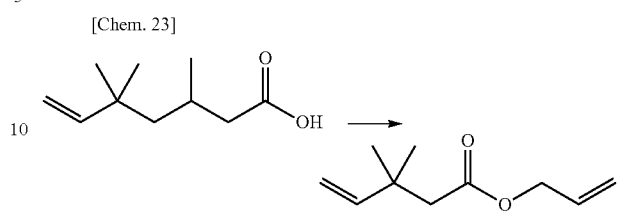

Into a 100-ml three-necked flask were charged, under nitrogen stream, allyl alcohol (20 g), para toluenesulfonic acid (0.1 g) and the 3,5,5-trimethylhept-6-enoic acid (2.0 g) obtained in Synthesis Example 10, followed by initiating heating on an oil bath set at 130° C. After refluxing for 3 hours, the reaction solution was cooled to the internal temperature of 40° C., and an aqueous 5% sodium hydrogen carbonate solution (5 g) was added thereto to neutralize, followed by performing recovery of the excess allyl alcohol under a reduced pressure. The condensate was diluted with n-heptane (20 ml), washed twice with water (10 ml), and then solvent recovery was performed under a reduced pressure. The resulting condensate was purified by silica gel column chromatography, thereby obtaining 1.3 g (purity: 93.3%) of allyl 3,5,5-trimethylhept-6-enoate shown by the formula above.

Physical data of allyl 3,5,5-trimethylhept-6-enoate

GC/MS m/z (%): 210 (1), 195 (1), 169 (2), 152 (4), 141 (6), 123 (5), 109 (26), 95 (15), 83 (10), 69 (85), 55 (28), 41 (100).

$^1$H NMR (500 MHz, CDCl$_3$) δ: 0.95 (3H, d), 1.01 (6H, s), 1.21-1.25 (1H, m), 1.34-1.38 (1H, m), 1.97-2.06 (1H, m), 2.09-2.14 (1H, m), 2.34-2.38 (1H, m), 4.56-4.57 (2H, m), 4.89-4.94 (2H, m), 5.21-5.24 (1H, m), 5.29-5.33 (1H, m), 5.76-5.82 (1H, m), 5.88-5.96 (1H, m).

$^{13}$C NMR (125 MHz, CDCl$_3$) δ: 22.3, 27.1, 27.3, 27.4, 37.0, 43.4, 49.4, 64.8, 110.4, 118.1, 132.4, 148.6, 172.7.

[Synthesis Example 12] Synthesis of 3,5,5-trimethylhept-6-en-1-ol

[Chem. 24]

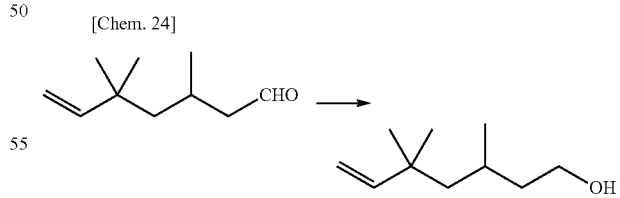

Into a 50-ml two-necked flask were charged sodium borohydride (0.074 g), tetrahydrofuran (2.5 ml) and methanol (0.5 ml) under nitrogen stream, followed by initiating stirring and cooling by an ice bath. Then, the (+)-3,5,5-trimethylhept-6-enal (0.67 g) obtained in Synthesis Example 3 was dropwise added thereto, followed by stirring for 30 minutes while cooling with ice. A 10% aqueous hydrochloric acid (1.8 g) was gradually added thereto, then n-hexane (5 ml) was added thereto, and after stirring for 5 minutes, the aqueous layer portion was separated. The organic layer was washed three-times with a 10% aqueous sodium chloride (3 g) and then solvent recovery was performed under a reduced pressure. The resulting crude product was purified by silica gel column chromatography, thereby obtaining 0.55 g (purity: 99.0%) of 3,5,5-trimethylhept-6-en-1-ol shown by the formula above.

Physical data of 3,5,5-trimethylhept-6-en-1-ol

GC/MS m/z (%): 156 (1), 138 (1), 123 (10), 109 (10), 95 (21), 81 (22), 69 (100), 55 (39), 41 (57).
$^1$H NMR (500 MHz, CDCl$_3$) δ: 0.91 (3H, d), 1.00 (6H, s) 1.16-1.20 (1H, m), 1.31-1.35 (2H, m), 1.36-1.42 (1H, m), 1.53-1.60 (2H, m), 3.63-3.68 (2H, m), 4.89-4.93 (2H, m), 5.77-5.80 (1H, m).
$^{13}$C NMR (125 MHz, CDCl$_3$) δ: 22.4, 25.9, 27.2, 27.4, 37.2, 41.9, 50.1, 61.1, 110.1, 148.9.

[Synthesis Example 13] Synthesis of 3,5,5-trimethylhept-6-enyl acetate

[Chem. 25]

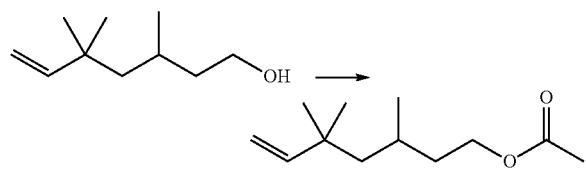

Into a 100-ml three-necked flask were charged 3,5,5-trimethylhept-6-en-1-ol (2.0 g) obtained by the method described in Synthesis Example 12, triethylamine (1.8 g) and toluene (10 ml) under nitrogen stream, followed by initiating stirring and cooling by an ice bath. Then, acetyl chloride (1.1 g) was dropwise added thereto while maintaining the internal temperature at 5° C. or less, followed by stirring for one hour. To the reaction solution was added water (10 ml), followed by stirring for 5 minutes, and the aqueous layer portion was separated. The organic layer was washed with water (10 ml) and then solvent recovery was performed under a reduced pressure. The resulting condensate was purified by silica gel column chromatography, thereby obtaining 1.90 g (purity: 99.8%) of 3,5,5-trimethyl-6-heptenyl acetate shown by the formula above.

Physical data of 3,5,5-trimethylhept-6-enyl acetate

GC/MS m/z (%): 138 (2), 123 (21), 109 (20), 95 (39), 81 (34), 69 (100), 55 (41), 43 (93).
$^1$H NMR (500 MHz, CDCl$_3$) δ: 0.91 (3H, d), 0.99 (6H, s) 1.16-1.20 (1H, m), 1.31-1.34 (1H, m), 1.38-1.45 (1H, m), 1.52-1.66 (2H, m), 2.03 (3H, s), 4.01-4.10 (2H, m), 4.88-4.92 (2H, m), 5.75-5.81 (1H, m).
$^{13}$C NMR (125 MHz, CDCl$_3$) δ: 21.0, 22.2, 26.3, 27.2, 27.4, 37.1, 37.4, 49.9, 62.9, 110.1, 148.7, 171.2.

Example 1

With respect to the compounds synthesized in Synthesis Examples 3, 5 to 9 and 11 to 13, evaluation of odor note was performed. The compounds in Synthesis Examples 6 to 9 and 11 to 13 are ones synthesized from the compound in Synthesis Example 3.

The evaluation of odor note was performed for the compound alone or in the form of flavor composition and/or fragrance composition, if desired, by five trained expert panelists, and character of the odor which each of the compounds had, for example, "floral-like", "green-like" or "citrus-like" was judged. The results are shown in Table 1.

TABLE 1

| Synthesis Example | Structural Formula | Odor Note |
|---|---|---|
| 3 | (+)-Form ...CHO | Green, Floral, Ozone |
| 5 | (−)-Form ...CHO | Green, Herb-like |
| 6 | ...NHOH | Green, Floral |
| 7 | ...CN | Green, Herb-like, Citrus |
| 8 | ...O/O (diethyl acetal) | Floral, Green |
| 9 | ...CHO | Green, Fruity |
| 11 | ...allyl ester | Fruity, Floral, Quince-like |
| 12 | ...OH | Floral, Green, Rose |
| 13 | ...OAc | Fruity, Violet, Woody |

Example 2

A fragrance composition for shampoo having the prescription shown in Table 2 below was prepared using the (+)-3,5,5-trimethylhept-6-enal shown in Synthesis Example 3.

TABLE 2

| Prescription | Parts by Mass |
|---|---|
| Allyl 2-pentyloxyglycolate | 10 |
| Allyl enanthate | 20 |
| Benzyl acetate | 60 |
| Damascenone | 1 |
| Dihydromyrcenol | 80 |
| Ethyl 2-methylbutyrate | 6 |

TABLE 2-continued

| Prescription | Parts by Mass |
|---|---|
| GALAXOLIDE 50BB (produced by International Flavors & Fragrances Inc.) | 100 |
| Geraniol | 20 |
| Methyl dihydrojasmonate | 200 |
| cis-3-Hexenyl acetate | 4 |
| cis-3-Hexenyl salicylate | 20 |
| cis-3-Hexenol | 4 |
| α-Hexylcinnamic aldehyde | 80 |
| β-Ionone | 20 |
| Lemon oil | 100 |
| p-t-Butyl-α-methyl hydrocinnamic aldehyde | 100 |
| ORBITONE (produced by Takasago International Corp.) | 60 |
| γ-Undecalactone | 20 |
| 4-Methyl-3-decen-5-ol | 10 |
| o-t-Butylcyclohexyl acetate | 80 |
| (+)-3,5,5-Trimethylhept-6-enal | 5 |
| Total | 1,000 |

As a Comparative Example, a fragrance composition for shampoo was prepared according to a prescription in which only the (+)-3,5,5-trimethylhept-6-enal was eliminated from the prescription shown in Table 2 above.

With respect to the two kinds of the fragrance compositions for shampoo prepared as described above, comparative test of odor was performed by five expert panelists in the form of the fragrance composition alone and in the form where the fragrance was practically imparted to the shampoo. As a result of comparing the aromas of the two, all of the panelists replied that by using the (+)-3,5,5-trimethylhept-6-enal, a highly preferred green- and floral-like scents could be imparted in comparison with the case of no addition, and also the aroma quality and strength were excellent.

Example 3

A fragrance composition for soap having the prescription shown in Table 3 below was prepared using the 3,5,5-trimethylhept-6-ene nitrile shown in Synthesis Example 7.

TABLE 3

| Prescription | Parts by Mass |
|---|---|
| Undecyl aldehyde | 2 |
| Dodecyl aldehyde | 1 |
| Isoamyl salicylate | 80 |
| Citronellol | 350 |
| Tricyclodecenyl propionate | 60 |
| Diphenyl oxide | 5 |
| α-Hexylcinnamic aldehyde | 70 |
| HINDINOL (produced by Takasago International Corp.) | 20 |
| β-Ionone | 10 |
| ORBITONE (produced by Takasago International Corp.) | 35 |
| Patchouli oil | 30 |
| Phenylethyl alcohol | 80 |
| Terpineol | 150 |
| p-t-Butylcyclohexyl acetate | 100 |
| β-Naphthyl methyl ether | 5 |
| 3,5,5-Trimethylhept-6-ene nitrile | 2 |
| Total | 1,000 |

As a Comparative Example, a fragrance composition for soap was prepared according to a prescription in which only the 3,5,5-trimethylhept-6-ene nitrile was eliminated from the prescription shown in Table 3 above.

With respect to the two kinds of the fragrance compositions for soap prepared as described above, comparative test of aroma was performed by four expert panelists in the form of the fragrance composition alone and in the form where the fragrance was practically imparted to the soap. As a result of comparing the aromas of the two, all of the panelists replied that by using the 3,5,5-trimethylhept-6-ene nitrile, a highly preferred green- and herb-like aromas could be imparted in comparison with the case of no addition, and also the aroma quality and strength were excellent.

While the present invention has been described in detail and with reference to specific embodiments thereof, it will be apparent to one skilled in the art that various changes and modifications can be made therein without departing from the spirit and scope of the present invention. The present application is based on a Japanese patent application filed on Jun. 4, 2014 (Application No. 2014-116076), the contents thereof being incorporated herein by reference.

The invention claimed is:

1. A method for improving a scent of a flavor and/or fragrance, comprising adding (+)-3,5,5-trimethylhept-6-enal.

* * * * *